United States Patent [19]

Lihme et al.

[11] Patent Number: 5,543,332

[45] Date of Patent: Aug. 6, 1996

[54] WATER-SOLUBLE, POLYMER-BASED REAGENTS AND CONJUGATES COMPRISING MOIETIES DERIVED FROM DIVINYL SULFONE

[75] Inventors: Allan O. F. Lihme, Birkerød, Denmark; Thomas Boenisch, Goleta, Calif.

[73] Assignee: Immunodex K/S, Glostrup, Denmark

[21] Appl. No.: 789,757

[22] Filed: Nov. 8, 1991

[30] Foreign Application Priority Data

Jul. 4, 1991 [DK] Denmark .................................. 1309/91

[51] Int. Cl.$^6$ .................................................. G01N 33/536
[52] U.S. Cl. .......................... 436/528; 436/529; 436/530; 436/531; 436/532; 436/823; 436/828; 530/391.1; 530/411; 530/813; 530/814; 530/816
[58] Field of Search .................................. 536/1.1, 30, 45, 536/51, 52, 56, 102, 112, 114; 525/54.1, 59,291; 436/529, 530, 531, 532, 823, 828, 528; 530/411, 391.1, 813, 814, 816

[56] References Cited

U.S. PATENT DOCUMENTS

| | | | |
|---|---|---|---|
| 3,788,948 | 1/1974 | Kagedal et al. | 195/68 |
| 3,853,987 | 12/1974 | Dreyer | 424/1 |
| 3,959,251 | 5/1976 | Porath et al. | 260/209 R |
| 4,061,736 | 12/1977 | Morris et al. | 424/177 |
| 4,108,972 | 8/1978 | Dreyer | 424/1 |
| 4,147,764 | 4/1979 | Levy et al. | 424/1.1 |
| 4,153,411 | 5/1979 | Schall, Jr. | 424/1 |
| 4,166,105 | 8/1979 | Hirschfeld | 424/8 |
| 4,169,137 | 9/1979 | Hirschfeld et al. | 424/8 |
| 4,174,384 | 11/1979 | Ullman et al. | 424/8 |
| 4,199,559 | 4/1980 | Ullman et al. | 424/8 |
| 4,207,200 | 6/1980 | Müller et al. | 252/184 |
| 4,254,096 | 3/1981 | Monthony et al. | 424/8 |
| 4,303,786 | 12/1981 | Goldstein et al. | 536/51 |
| 4,452,886 | 6/1984 | Henry | 435/7 |
| 4,645,646 | 2/1987 | Gadow et al. | 422/61 |
| 4,696,980 | 9/1987 | Porath | 525/326.1 |
| 4,698,387 | 10/1987 | Schmidt et al. | 530/402 |
| 4,752,339 | 6/1988 | Kohn | 106/208 |
| 4,780,409 | 10/1988 | Monji et al. | 435/7.1 |
| 4,885,207 | 12/1989 | Johnson et al. | 428/403 |
| 5,015,268 | 5/1991 | Ho | 55/16 |
| 5,062,866 | 11/1991 | Ho | 55/16 |

FOREIGN PATENT DOCUMENTS

| | | | |
|---|---|---|---|
| 0010405 | 4/1980 | European Pat. Off. | G01N 33/54 |
| 10011837 | 6/1980 | European Pat. Off. | G01N 33/537 |
| 0077671A1 | 4/1983 | European Pat. Off. | G01N 33/54 |
| 0077671B1 | 4/1983 | European Pat. Off. | G01N 33/532 |
| 0135071 | 4/1985 | European Pat. Off. | G01N 33/533 |
| 0155224A3 | 9/1985 | European Pat. Off. | G01N 33/543 |
| 20245926 | 11/1987 | European Pat. Off. | G01N 33/543 |
| 20268296 | 5/1988 | European Pat. Off. | G01N 33/536 |
| 0323692 | 7/1989 | European Pat. Off. | G01N 33/546 |
| 20326100 | 8/1989 | European Pat. Off. | G01N 33/537 |
| 10406473 | 1/1991 | European Pat. Off. | G01N 33/538 |
| 2453847 | 7/1980 | France | C01C 101/00 |
| 361320 | 9/1973 | Sweden | C07G 7/02 |

OTHER PUBLICATIONS

Porath et al. (1975) "Agar derivatives for chromatography, electrophoresis and gel–bound enzymes III. Rigid Gel Agarose gels cross–linked with divinyl sulfone (DVS)" J. Chromatography 103: 49–62.

Young et al. (1978) "Preparation of affinity chromatography media from soluble polysaccharides by cross–linkage with divinyl sulfone" Carbohydrate Res 66: 299–302.

Porath (1974) "General Methods and Coupling Procedures" Methods Enzymol 34: 13–30

Porath et al. (1985) "Thiophilic adsorption–a new method for protein fractionation" FEBS 185(2): 306–310.

Porath et al. (1972) "High Capacity Chemisorbents for Protein Immobilization" Nature New Biol. 238: 261–262.

Allen et al. (1977) "A Simple Procedure for the Isolation of L–Fulose"–Binding Lectins from *Ulex europaeus* and *Lotustetragonolobus* Carbohydrate Res. 58: 253–265.

Sairan (1981) "Isolation of Hormonal Proteins and Antibodies by Affinity Chromatography" J. Chromatography 215: 143–152.

Luong et al., "Recent development in downstream processing based on affinity interactions", TIBTECH, vol. 5, 1987.

Fujii et al., "Application of reversibly soluble polymers in bioprocessing", TIBTECH, vol. 9, 1991.

Naish et al., *Handbook, Immunochemical Staining Methods*, DAKO Corp., 1989.

C. Kendall *et al.*, *J. Immunological Methods*, "Utilization of the Biotin/Avidin System to Amplify the Sensitivity of the Enzyme–Linked Immunosorbent Assay (ELISA)", 56 (1983) pp. 329–339.

J. Carlsson, *Biochem. J.*, "Protein Thiolation and reversible Protein–Protein Conjugation", (1978) 173, pp. 723–737.

A. Johnstone *et al.*, *Immunochemistry in Practice*, 2nd Ed., (1987) 55–63. Blackwell Scientific Publications.

J. Porath *et al.*, *J. Chromatogr.*, "AGAR Derivatives for Chromatography, Electrophoresis and Gel–Bound Enzymes", 103 (1975) 49–62.

Wileman *et al.*, *J. Pharm. Pharmacol*, "soluble Asparaginase–Dextran Conjugates Show Increased Circulatory Persistence and Lowered Antigen Reactivity", 38 (1986) 264–271.

Young et al, *Chemical Abstracts*, vol. 90, No. 5, Jan. 29, 1979, Abstract No. 35749.

Lihme et al., *Journal of Chromatography*, 376, (1986), pp. 299–305.

Schall et al., *Clinical Chemistry*, vol. 27, No. 7, (1981), pp. 1157–1164.

*Primary Examiner*—Mary E. Ceperley
*Attorney, Agent, or Firm*—Foley & Lardner

[57] ABSTRACT

Water soluble reagents are claimed, comprising a water-soluble polymeric carrier molecule having attached thereto more than one connecting moiety wherein the connecting moiety is derived from divinyl sulfone, and wherein each connecting moiety is attached to a reactive functional group on the polymeric molecule, and wherein the reagents are capable of reaction with a molecular species having a functional group which is reactive towards the terminal vinyl group of the more than one connecting moiety and the molecular species is selected from the group consisting of labelling species, marking species, and targeting species.

15 Claims, 8 Drawing Sheets

WATER-SOLUBLE, POLYMER-BASED REAGENTS AND CONJUGATES COMPRISING MOIETIES DERIVED FROM DIVINYL SULFONE

The present invention relates to water-soluble reagents and conjugates which are particularly well suited for use, for example, in biologically relevant detection, quantification and targetting procedures, e.g. in the fields of immunohistochemistry, detection of immunoreactive species, antibody immobilisation, separation or purification, DNA hybridization tests and flow cytometry, as well as other applications which will become apparent on the basis of the disclosure in the present specification.

The reagents and conjugates of the invention are based on water-soluble, polymeric carrier molecules having moderate to high molecular weight and to which are covalently coupled reactive divinyl-sulfone-derived moieties [i.e. moieties having a free ("dangling"), terminal, reactive vinyl group] or bridging divinyl-sulfone-derived moieties.

The polymeric carrier molecules of particularly preferred reagents or conjugates according to the invention are initially non-cross-linked and are of essentially zero charge at pH values which are of relevance within the fields of application of the invention. Cross-linking does, however, generally occur in the course of reaction of the polymers with divinyl sulfone in a preparation process according to the invention. In the case of the presently most preferred polymeric carrier molecules, viz. dextrans, the present inventors have found that it is possible to vary the degree of cross-linking in a reproducible manner and within rather wide limits, e.g. by regulating reaction time, the dextran concentration or the pH in the medium (or a combination of these) during the preparation process.

The preparation of the reagents and conjugates of the invention takes under generally mild conditions and using generally straight-forward procedures which, as indicated above, constitute aspects of the present invention. Under appropriate storage conditions, many of the reagents and conjugates according to the invention, and notably the chemically reactive reagents and conjugates according to the invention (i.e. reagents and conjugates which react readily with certain types of functional groups present in molecular species so as to form covalent bonds anchoring the molecular species in question to the polymeric carrier reagents) display remarkable and unexpected stability ("shelf-life") during prolonged storage in solution, rendering the commercialisation of pre-prepared reagents and conjugates of these types perfectly feasible.

BACKGROUND OF THE INVENTION

The last two decades have seen vast progress in the fields of immunochemistry and molecular biology, and this is clearly reflected in the volume of relevant scientific and patent literature appearing during this period. Among areas for which the present invention is of relevance, an area of particular growth has, for example, been that of qualitative and/or quantitative assays involving the use of immunoreactive species, i.e. antigens, haptens or antibodies.

One such area is that of immunohistochemical/cytochemical detection procedures, the purpose of which is normally the localization of antigenic determinants present in tissues or in/on cells via immunochemical reaction of these antigenic determinants with specific so-called primary antibodies which react only with the target antigenic determinants. The primary antibodies are either labelled with appropriate labels (e.g. enzymes, fluorescent groups or heavy atoms), or they are themselves further detected via an immunochemical reaction with specific so-called secondary antibodies which react with the primary antibodies; in the latter case it is the secondary antibodies which are labelled with appropriate labels (e.g. enzymes, fluorescent groups or heavy atoms). Alternatively, the immunochemical reaction between target antigenic determinants and primary antibodies is detected via an immunochemical reaction with a specific so-called link antibody which has the property of reacting simultaneously with (i) the primary antibodies and (ii) an antibody to which enzymes have been attached via an immunochemical reaction or via covalent coupling.

As a further alternative, the immunochemical reaction between target antigenic determinants and primary antibodies, or between primary antibodies and secondary antibodies, is detected by exploiting the binding which occurs between certain pairs of complementary molecules other than antigens and antibodies; an example of such a complementary pair is biotin and streptavidin. In this approach, one member of the complementary pair is attached to the primary or secondary antibodies and the other molecule is combined with suitable labels (e.g. enzymes, fluorescent groups or heavy atoms).

In procedures of this type, a specimen in the form of a sample of thinly cut tissue or a sample of cells (typically from a body fluid) is affixed to a glass slide. The applied specimen is then normally treated with various chemicals to facilitate the subsequent immunochemical reactions. The specimen is then subjected to treatment with a labelled or non-labelled primary antibody, as appropriate, whereupon the antibody becomes immunochemically bound to the antigen in question in/on the specimen. After removal of excess antibody by suitable washing of the specimen, the antibody bound to the antigenic determinant is detected by treatment with appropriate reagents, depending on the choice of the visualization system (as described previously, above) in conjunction with suitable washing procedures. After removal (by washing) of the excess labelled reagent from the chosen visualization system, the specimen is subjected to a treatment as follows, depending on the label in question:

(i) in the case of enzyme labels, the specimen is treated with a substrate (colour developing reagent). The enzyme reacts with the substrate, leading to the formation of a coloured insoluble deposit at and around the location of the enzyme;

(ii) in the case of a heavy metal label such as gold, the specimen can be treated with a so-called enhancement reagent containing silver. Silver metal is then precipitated as a black deposit at and around the location of the gold.

(iii) in the case of fluorescent labels a developing reagent is normally not needed.

After a washing step, some of the constituents of the specimen can then be coloured by a chemical dye which gives a suitable contrast to the colour given by the label in question. After a final washing step, the specimen is coated with a transparent reagent to ensure a permanent record for the examination.

The visualization of the labels (indirectly expressing the localization and amount of target antigenic determinants) is performed as follows:

(i) light microscopic examination (in the case of enzyme labels);

(ii) light or electron microscopic examination (in the case of heavy metal labels);

(iii) fluorescence microscopic examination, using irradiated light of a suitable wavelength (in the case of fluorescent labels).

The period in question has also seen, for example, the emergence and development of assays of the so-called ELISA (Enzyme-Linked Immuno-Sorbent Assay) type, in which an antigen, hapten or antibody is detected by means of an enzyme which is covalently coupled (also denoted linked or conjugated) either (when an antigen or hapten is to be determined) to an antibody which is specific for the antigen or hapten in question, or (when an antibody is to be determined) to an antibody which is specific for the antibody in question. In "traditional" ELISA, the antigen, hapten (the latter generally in the form of a conjugate with, e.g., a protein) or antibody to be detected/determined is normally bound or immobilized by allowing it to bind immunochemically to (i) a so-called "catching" antibody in the case of antigen or hapten determination or (ii) an antigen in the case of antibody determination, each of which is attached (generally by non-covalent adsorption) to the surface of an appropriate material, such as polystyrene in the form of beads or microtiter trays, and the appropriate enzyme-linked specific antibody is then allowed to bind to the immobilized species which is to be detected/determined; the amount of bound specific antibody, and thus the amount of immobilized species, is then determined by adding a substance which is a substrate for the linked enzyme and which, upon enzymatic decomposition, results in the development of a characteristic colour, the intensity of which (measured, for example, by spectrophotometry or simple colorimetry/comparimetry) is thus related (normally proportional) to the quantity of the species of interest which is to be determined. Examples of preferred enzymes for use in assays of this type (as well as in immunohistochemical procedures) are peroxidases, e.g. horseradish peroxidase, alkaline phosphatase, glucose oxidases, galactosidases and ureases.

Immunochemical assays of a type analogous to ELISA but employing other means of detection, e.g. the use of specific antibodies to which fluorescent or luminescent marker molecules are covalently linked, have also undergone considerable development in the same period, and the emergence of so-called "time-resolved fluorescence" is a good example: In this technique the marker or label is generally either $Eu^{3+}$ or a europium chelator (although certain other lanthanide species or lanthanide chelators have also been employed), and a fluorescent europium chelate can then be formed by adding an organic chelator or $Eu^{3+}$, respectively. In contrast to most of the more traditional fluorescent marker species, e.g. fluorescein, which generally have fluorescence lifetimes of about 100 nanoseconds (nsec) or less, the fluorescence lifetime of lanthanide chelates is generally in the range of 100–1000 microseconds (μsec); by making use of a pulsed light source and a time-gated fluorometer, the fluorescence of these compounds can be measured in a time-window of about 200–600 μsec after each excitation. A main advantage of this technique is the reduction of background signals which may arise from short-lived fluorescence of other substances present, for example, in the analysis sample, in or on the material of microtiter wells, in cuvettes or the like, or elsewhere in the measurement system.

A further group of procedures which employ immunochemical detection techniques, and which should be mentioned in the context of the invention, are "immunoblotting" procedures, examples of which are the so-called "dot blot" and "western blot" procedures: In the western blot procedure, which is employed for the analysis and identification of antigenic polypeptides or proteins, the proteins/polypeptides in a mixture thereof are separated by polyacrylamide gel electrophoresis and then transferred electrophoretically ("blotted") to a sheet of nitrocellulose or chemically treated paper to which the proteins/polypeptides bind in a pattern identical to that in the gel. The appropriate specific antibody is then added, followed by a labelled second antibody against the first antibody or labelled protein-A (labelled with, for example, a radioisotope, fluorescent dye, enzyme or colloidal gold). The location of the label (and thus the presence of the particular antigen) is then detected in the appropriate manner outlined previously.

As far as developments in the general field of molecular biology are concerned, one non-immunochemical area of significance has been that of hybridization techniques in connection with gene structure analysis: In "traditional" hybridization techniques, a particular nucleotide sequence (also known as a "probe" or "gene probe") is labelled with an appropriate marker or label, e.g. a radioactive isotope, and is then added to a sample of a nucleic acid of interest, e.g. a sample in the form of part of intact cells or in the form of isolated DNA or RNA fragments. The sample can either be free in solution or immobilized on a solid-phase substrate. If the probe and the nucleic acid sample hybridize by formation of a strong, non-covalent bond between them, it can reasonably be assumed that a nucleotide sequence essentially identical to that of the probe is present in the nucleic acid. The marker or label on the probe thus provides a means of establishing whether hybridization has occurred, and for determining the amount of DNA/RNA sample present.

The so-called "Southern blot" method for the detection of rare DNA fragments in a complex mixture of DNA is an example of a procedure employing the technique of hybridization: Gel electrophoresis is used to separate the various fragments, which are then denatured and transferred by blotting to nitrocellulose sheet. The fragments are then hybridized to an appropriate radioactively labelled probe, and their position is revealed by autoradiography. Analogous procedures have been devised for RNA and, as already mentioned ("western blot", vide supra), for protein or peptide antigens.

Hybridization techniques have been of great importance in biochemical genetics for an understanding of the relationship between nucleotide sequences and their function, and they provide an important diagnostic tool for the detection, for example, of genetic defects, or of infectious agents such as viruses or bacteria.

Owing primarily to the health hazards posed by the use of radioisotopes in hybridization procedures of the above types, attempts have been made to replace them with more innocuous (and, generally, more readily available) markers or labels. However, attempts made until now, for example using biotinylated probes to be detected by means of, e.g., enzyme-labelled reagents, have resulted in attendant loss of sensitivity relative to that obtainable using radioactively labelled probes.

The above-mentioned problem of poor detection sensitivity when using, in particular, non-radioactive labels, applies not only to hybridization techniques, but also to immunochemical detection or assay procedures or when immunochemical detection is used to amplify a hybridization reaction. In other words, the lower detection limit may prove to be inadequate for the unambiguous detection or accurate quantitative determination of low levels of, e.g., antigens or antibodies or nucleic acids. This may, for example, be due to the intensity of colour or fluorescence in an immunochemical or hybridization procedure of one of the above-mentioned types being too low, chiefly as a consequence of the fact that normally only one or, at best, a very few (generally less than five) molecules of enzyme or marker species can be linked, e.g., to each specific antibody molecule or to each molecule of the nucleotide sequence of the probe. Furthermore, for each marker species which is attached (conjugated) to, e.g., an antibody molecule, and particularly if the marker species impart a net positive or negative charge to the antibody/marker conjugate, there is an increasing risk of a deleterious influence on the natural ability of, for example, the antibody to participate in the correct immunochemical binding reaction of interest; furthermore, the presence of a net positive or negative charge on such a conjugate increases the risk of undesirable non-specific binding of the conjugate to other materials or species in the system.

In the immunochemical field in particular, considerable effort has been devoted to devising ways to enhance the sensitivity of immunochemical assay procedures, and one approach which has achieved a good measure of success involves the attachment of an immunochemically reactive species, e.g. an antibody, and a plurality of enzyme molecules, fluorescent marker molecules or the like to one and the same backbone or carrier, e.g. polymeric carrier. There are numerous patent documents relating to this kind of approach, and making use of either soluble or insoluble carriers. Generally speaking, in applications of the type outlined above, the use of soluble carriers is to be preferred, since the presence of the carrier (with the coupled immunochemically reactive species and enzymes/marker molecules or the like) in homogeneous solution rather than as a heterogeneous phase, together with the relatively great conformational flexibility of such species in the solution phase, vastly enhances the rate and, in general, the extent of immunochemical reactivity with the immunochemical counterpart species which is to be detected or determined; in immunohistochemical applications the use of soluble carriers is virtually essential, since good tissue contact or penetration is necessary in order to ensure optimal access to the immunochemically reactive moieties or epitopes located on or within the tissue. Moreover, it is generally much easier to remove (e.g. by washing or flushing) carrier-borne immunochemically reactive species, e.g. carrier-borne antibodies, which have not (e.g. owing to "saturation" of available binding sites) become bound to immunochemical counterparts, e.g. to antigens attached, for example, to the surface of an microtiter tray, immunoplate or the like, when the carrier-borne species in question are soluble than when they are insoluble or colloidal.

The present invention represents a significant advance with respect, inter alia, to the enhancement of flexibility, sensitivity and reliability of all of the various types of detection and assay procedures outlined by way of example above. The invention can also be exploited, for example, to reduce—without loss of sensitivity—the number of successive "layers" of immunoreactive components (antigen, antibody, anti-antibody etc) which would otherwise be required in the performance of, e.g., a traditional ELISA or histochemical procedure. Other advantages associated with the invention will become apparent from the present specification and the working examples given herein.

Since the present invention relates, as already indicated, to water-soluble reagents and conjugates, and to their preparation and use, the following outline of a number of pertinent patent documents is confined to disclosures in which soluble carriers are employed:

European patent 0 077 671 relates inter alia to a water-soluble, non-cross-linked and non-primary-amine-containing polymer to which is conjugated a marker substance. The polymer/marker substance conjugate has a negative or zero charge, and to the polymer part of each molecule thereof there is attached "only one immunological homologue" (antigen or antibody). The original European patent application (EP 0 077 671 A1) does not restrict itself to "only one" immunological homologue molecule, but neither is there any specific mention of more than one immunological homologue. The preferred water-soluble polymers in the latter patent/patent application are polyacrylic acid, polymethacrylic acid, polyacrylamide, polyvinyl alcohol, polyallyl alcohol, polymer combinations of the foregoing, hydroxyethyl-cellulose, hydroxypropyl-cellulose, natural water-soluble polymers and synthetic water-soluble polymers. The molecules of marker substance may be incorporated ab initio in the polymer by co-polymerizing a relatively small percentage of a suitable monomer incorporating the marker substance (e.g., in the case of a fluorescent marker substance, a monomer produced by the reaction of fluoresceinamine with acryloyl chloride in equimolar amounts) with the monomers which form the basis of the polymer backbone (e.g. acrylic acid and acrylamide). Other mentioned methods for attachment of marker substances to the polymer include making use of an activated group on the marker substance, and employing an "external activating agent". As regards the attachment of the immunological homologue to the polymer backbone, the following examples are given:

(i) an acrylic acid/acrylamide copolymer incorporating ca. 1% of a copolymerized monomer produced by reaction of fluoresceinamine with acryloyl chloride is activated by reaction with carbonyl diimidazole and N-hydroxysuccinimide, and the resulting activated polymer/marker substance conjugate is then reacted with a monoclonal antibody;

(ii) a monoclonal antibody which has been biotinylated by reaction with biotinyl-N-hydroxysuccinimide is added to a conjugate formed by reaction of avidin with the activated polymer/marker substance conjugate prepared as outlined in (i), above; attachment of the monoclonal antibody to the polymer backbone in this case is via the strong, but non-covalent, binding interaction between the biotin groups covalently bound to the antibody, and avidin moieties covalently conjugated to the polymer/marker substance.

There appears to be no disclosure in this patent relating to the use of dextrans as the polymer carrier, or of divinyl sulfone, or a moiety derived therefrom, as an activating reagent or coupling/bridging moiety via which a marker substance or an immunological homologue may be attached to the polymer.

U.S. Pat. No. 4,152,411 relates to a labelled "spine tool" for determination of a component of the antigen/antibody reaction, preferably making use of polymers with amide bonds between the individual units of the polymer, for example polylysine, other homopoly(amino acids) or polypeptides; on average, only one molecule (hapten, antigen or antibody) to be "labelled" is attached to the polymer "spine tool". The specification mentions tolylene-2,4-diisocyanate, glutaraldehyde and carbodiimide as candidates for activation reagents by which the molecule to be "labelled" may be coupled to the polymer carrier, and two specific examples illustrate the use of 1-ethyl-3-(3-dimethyl-aminopropyl)-carbodiimide for the coupling of a hapten, viz. thyroxine. Whilst a number of possible labelling or marker species are mentioned, including numerous fluorescent substances (such as fluorescein) and enzymes (such as peroxidases), details of the manner in which these are to be attached to the polymer carrier are given only in the case of one specific enzyme, namely horseradish peroxidase (HRP), which in the example in question is coupled to polylysine/thyroxine conjugate via the initial oxidation of the diol moiety of HRP using sodium periodate; the resulting diketone moiety of the oxidized HRP is then allowed to react with the latter conjugate (via an amino function of the polylysine part) to form a Schiff base intermediate, which in turn is then reduced, e.g. using sodium borohydride, to give the HRP-labelled polylysine/thyroxine conjugate. This particular type of labelled conjugate ("diagnostic marker spine tool") is stated as being " . . . amazingly stable upon storage for extended periods. It is considered feasible to store such a tool for up to three or six months or more in inert atmosphere, e.g. under nitrogen, and in the absence of moisture."

The possibility of using polysaccharides, including dextran, as the basis for the "spine tool" is briefly mentioned in the specification, but there is no indication of the detailed manner in which attachment of the molecules of interest to dextran should take place. Neither is there any indication of any advantages associated with the use of dextran for this purpose.

EP 0 010 405 A1 relates, inter alia, to an immunochemical assay reagent comprising a carboxyl-containing, water-soluble, mono-olefinic polymeric compound combined (i.e. coupled) with a hapten or a chemically modified product thereof, and to a method for the immunochemical determination of a hapten using such a reagent. There appears to be no mention of the use of polymers related to dextran in the context of this patent application.

Chemical strategies which are mentioned in connection with the coupling of a hapten to the polymeric compound are: the use of carbodiimides (e.g. dicyclohexylcarbodiimide), carbonyldiimidazole or diphenylphosphoryl azide (DPPA); and the intermediate formation of mixed acid anhydrides (formed, e.g., using a chloroformic acid ester such as isobutyl chloroformate), active esters (formed, e.g., using N-hydroxysuccinimide), azides (formed using hydrazine followed by nitrous acid) or acid chlorides (formed, e.g., using thionyl chloride or phosphorus oxychloride).

The immunochemical assay reagents in question show "very high stability in the form of an aqueous solution . . . and can fully withstand storage at room temperature".

There appears to be no mention of the possibility of coupling an immunologically active species (antigen, antibody) other than a hapten to the polymeric material in question.

U.S. Pat. Nos. 4,166,105 and 4,169,137 (to Hirschfeld and to Hirschfeld et al., respectively) relate to antigen-detecting reagents and dye-tagged reagents, respectively, comprising a primary amine-containing polyfunctional polymer backbone, e.g. a polyethyleneimine backbone, and attached marker molecules (such as a plurality of fluorescent dye molecules); the reagents according to the former patent further comprise an antibody specific for the antigen to be detected, whilst the reagents according to the latter patent further comprise a "first reactant", particularly an antibody. Working examples given in both patents demonstrate an average of at most one antibody molecule attached to the polymer backbone. The use of a dialdehyde, in particular glutaraldehyde, as coupling reagent for coupling marker molecules and antibody/first reactant to the polymer backbone is preferred, there being no mention of the possibility of using divinyl sulfone-based coupling.

EP 0 135 071 A2 relates, inter alia, to chemiluminescent-labelled hapten conjugates comprising a chemiluminescent group (e.g. a group derived from luminol or a derivative thereof), a chain polymeric "attachment group" (in German: Verknüpfungsgruppe) and a hapten; the attachment group has repeating functional groups, and for each mole of attachment group there are several moles of luminescent group and several moles of hapten, preferably at least 10 moles of each per mole of attachment group.

Examples of chain polymers which are briefly mentioned in the specification include peptides, proteins, glycoproteins, glycolipids and carbohydrates, including polysaccharides such as dextrans, and divinyl sulfone is briefly mentioned among examples of coupling reagents for coupling of chemiluminescent groups or haptens to repeating functional, reactive groups (Such as amino, carboxy, carbonyl, "thionyl" or hydroxy groups) on the polymer. However, the only working examples provided relate to the preparation and use, in a chemiluminescence assay, of luminol/hapten/protein conjugates based on the proteins (polymers) transferrin and porcine thyreoglobulin, and employing a carbodiimide and succinic anhydride, respectively, as coupling reagents for coupling of the haptens to the proteins.

There is no further disclosure nor any working example in this document relating to the use of, or any advantages associated with the use of, the coupling chemistry preferred in the context of the present invention, viz. coupling based on moieties derived from divinyl sulfone; neither does there appear to be any clear indication of the stability or shelf-life of the disclosed conjugates, either in the solid state or in solution.

In relation to the conjugates disclosed in the documents reviewed above, the reagents/conjugates according to the present invention distinguish themselves, for example, as described in the following:

Firstly, as is well documented by the working examples given herein (vide infra), water-soluble reagents and conjugates of the present invention have been found to possess unexpectedly and extraordinarily high stability/shelf life in aqueous solution at moderate (non-extreme) pH values, not only at low temperatures but also at temperatures somewhat above normal ambient temperatures. It is particularly noteworthy that this is true of:

(i) water-soluble reagents of the invention which have no molecular species [as defined herein; (vide infra)] coupled thereto, i.e. reagents of the invention which comprise a water-soluble polymeric carrier molecule to which there are covalently attached one or more groups or moieties derived from divinyl sulfone, one end of each of which is attached to the carrier molecule via a covalent linkage formed between one of the two vinyl groups of divinyl sulfone and a reactive functionality present on the carrier molecule, and the other end of which retains a free, "dangling" vinyl group which is capable of subsequent reaction with an appropriate molecular species having a suitably reactive functional group; and (ii) water-soluble conjugates of the invention which comprise a water-soluble polymeric carrier molecule to which are covalently attached, via linking groups derived from divinyl sulfone, one or more molecular species, the polymeric carrier molecule further having covalently attached thereto one or more divinyl-sulfone-derived moieties having a free, reactive vinyl group.

As documented in the working examples herein, the present inventors have found that the inherent reactivity of the free vinyl groups present in the latter types of water-soluble reagents and conjugates of the invention is suppressed at pH values close to neutrality, whereas these groups exhibit very high reactivity at alkaline pH values, e.g. at a pH in the region of about 9–11.

Furthermore, preliminary results obtained by the present inventors also indicate that water-soluble conjugates of the invention which are substantially "saturated" with respect to the possibility of covalent attachment of further molecular species (i.e. conjugates according to the invention which have molecular species covalently attached to the polymeric carrier molecule via linking groups derived from divinyl sulfone, but which substantially lack divinyl-sulfone-derived moieties having free, reactive vinyl groups) also possess similarly high stability/shelf life in aqueous solution at moderate pH values.

The above-described long-term stability exhibited by reagents and conjugates of the present invention thus makes it possible, as already indicated (vide supra), to market such reagents or conjugates in pre-prepared form, e.g. in the form of a kit which might include (where relevant) instructions and, possibly, supplementary chemical reagents for carrying out the appropriate further chemical procedures; the purchaser can thus (i) subsequently attach desired molecular species to pre-prepared, chemically reactive reagents or conjugates of the invention to prepare, for example, assay reagents or conjugates which are tailored to meet specific requirements, or (ii), in the case of pre-prepared, "saturated" conjugates (vide supra) according to the invention, use a pre-prepared conjugate according to the invention directly in a relevant detection or assay procedure.

Secondly, as is apparent from the working examples provided herein (vide infra), in relation to the size of the polymeric carrier molecule the reagents and conjugates according to the present invention, notably the most preferred reagents and conjugates of the invention in which the polymeric carrier molecule is a dextran, are capable of a high degree of loading with molecular species while at the same time remaining water-soluble. Furthermore, taking into account the relatively moderate content of reactive groups (i.e. reactive groups derived from divinyl sulfone, and via which covalent attachment of molecular species takes place) on the polymeric carrier molecules of the intermediate reagents employed in the present working examples in question, and given the fact that appreciably higher contents of reactive groups are, as is well documented in other working examples herein, attainable, it is envisaged that considerably higher levels of loading with molecular species are achievable, for example such that covalent attachment of several thousands of molecular species of low molecular weight, or up to of the order of a thousand molecular species of relatively high molecular weight, per carrier molecule is achievable, depending of course on the steric bulk and/or molecular weight of the molecular species in question, and on the size or molecular weight of the polymeric carrier molecule.

Thirdly, not only is loading of the carrier molecule with a plurality of, for example, hapten species (as in EP 0 135 071 A2) or fluorescein groups (as in U.S. Pat. No. 4,166,105 and U.S. Pat. No. 4,169,137) possible according to the present invention, but it is equally well possible to attach a plurality of molecules of antigens, antibodies, enzymes, gene probes, avidin or other types of molecular substances which will be apparent from the disclosure herein. Particularly noteworthy is the ability according to the invention to attach a plurality of antibodies to a water-soluble polymeric carrier molecule as employed within the context of the invention; on the basis of the patent and scientific literature known to the present inventors and relating to water-soluble reagents or conjugates of a type relevant in relation to the present invention, it would appear that there has either been technical prejudice with regard to the feasibility or desirability of achieving attachment of more than one antibody molecule (or, at best, more than a very few antibody molecules) to the carrier molecule, or, perhaps, that attempts to achieve this have generally failed. The use of an antibody-bearing conjugate according to the invention (bearing a plurality of antibodies and a plurality of suitable marker or label species) in an immunochemical assay, such as an immunohistochemical or ELISA-type assay enhances the speed of reaction and the sensitivity (and, probably, the accuracy and reliability) of such assays. It is believed that the attachment, according to the present invention, of a plurality of antibody molecules (e.g. about 5, 10, 15, 20 or more) to the polymer carrier or backbone leads to, for example: (a) increased statistical probability of obtaining a plurality of antibody molecules having the correct steric conformation for satisfactory binding to the complementary immunological component (such as an antigen), and (b) increased strength of binding to the complementary immunological component.

It may also be mentioned here that similar advantages are also believed to be attainable in application of the invention in, e.g., hybridization techniques (vide supra), in that detection sensitivity and reliability of such procedures is to be expected to be significantly enhanced by employing an appropriate conjugate according to the invention comprising a plurality of marker species and, possibly, a plurality of probe molecules.

Fourthly, and as a more general aspect, in preparing conjugates according to the present invention which comprise two different types of attached molecular species, the divinyl-sulfone-based coupling chemistry employed in the context of the invention, notably in combination with the use, in a manner according to the invention, of a lyotropic salt in the attachment of these molecular species, makes possible a very wide variation in the numbers of and/or ratio between the two types of molecular species which are attached to the polymeric carrier molecule: As already outlined above, the ability to regulate the reactivity of free vinyl groups in reagents or conjugates of the invention by varying the pH makes it possible to establish a desired level of loading of the polymeric carrier (in relation to the available number of reactive vinyl groups) with one of the molecular species in question, after which the inherent reactivity of the remaining, unreacted vinyl groups can be suppressed by adjustment of the pH of the medium; if desired, the "intermediate" conjugate may then be subjected to one or more purification procedures, e.g. by chromatographic means, before proceeding to attach the second type of molecular species of interest. Not only is it thus possible to prepare well-characterized conjugates, but it is also possible to exert a high degree of control of the preparation process in a straight-forward manner.

Fifthly, it is believed that conjugates according to the invention based on certain preferred types of polymeric carrier molecules, viz. polymeric carrier molecules which are substantially linear, possess tissue structure penetration properties in spite of a relatively high total molecular weight.

DETAILED DESCRIPTION OF THE INVENTION

In a first aspect, the present invention provides a water-soluble reagent comprising a water-soluble polymeric carrier molecule having covalently attached thereto one or more moieties derived from divinyl sulfone, each of which moieties is attached via a linkage formed between one of the two vinyl groups of a divinyl sulfone molecule and a reactive functionality on the polymeric carrier molecule, at least one such moiety in its attached state having the remaining vinyl group free and capable of reaction with a molecular species having a functional group which is reactive towards the free vinyl group.

The term "molecular species" in the context of the present invention is used to denote, for example: molecules or ionic species which serve as labels or markers (such as enzymes, or fluorescent or luminescent species); or molecules which serve as targetting species, i.e. molecules which are capable of binding selectively or specifically to one or more target molecules, moieties, receptors or epitopes (examples of such targetting species being haptens or hapten conjugates, antigens, antibodies, nucleotide sequences and hormones).

Owing to the nature of the coupling chemistry employed in the context of the present invention as a whole, including in methods according to the invention for preparing reagents and conjugates of the invention, i.e. the establishment, on the polymeric carrier molecule, of covalently bound reactive moieties deriving from divinyl sulfone, and the establishment of covalent bonds between, on the one hand, such moieties, and, on the other hand, molecular species as defined herein, the known pattern of reactivity of the vinyl groups in a species such as divinyl sulfone will generally require that the reactive functionality on the polymeric carrier, i.e. the group with which a vinyl group of, divinyl sulfone will react to form a covalent bond, is a nucleophilic function. Suitable polymeric carriers will then be, for example, polymeric carriers with functional groups such as: —O⁻ (e.g. deprotonated phenolic hydroxy groups, such as deprotonated aromatic hydroxy groups in tyrosine residues of polypeptides or proteins), —S⁻ (e.g. deprotonated thiol groups on aromatic rings or aliphatic groups, such as deprotonated thiol groups in cysteine residues of polypeptides or proteins), —OH (e.g. aliphatic hydroxy groups on sugar rings, such as glucose or other monosaccharide rings in oligo- or polysaccharides; or alcoholic hydroxy groups in polyols, such as polyethylene glycols; or hydroxy groups in certain amino acid residues of polypeptides or proteins, such as serine or threonine residues), —SH (e.g. thiol groups in cysteine residues of polypeptides or proteins), primary amino groups (e.g. in lysine or ornithine residues of polypeptides or proteins; or in amino-substituted sugar rings in certain polysaccharides or derivatives thereof, such as chitosan) or secondary amino groups (e.g. in histidine residues of polypeptides or proteins). For similar reasons, the functional group in question on molecular species in the context of the invention will also normally be a nucleophilic function, such as a nucleophilic function of one of the above-described types.

The water-soluble polymers which function as the carrier molecules in reagents and conjugates of the invention may be chosen from a wide variety of types of polymers, including:

natural and synthetic polysaccharides, as well as derivatives thereof, for example dextrans and dextran derivatives, starches and starch derivatives, cellulose derivatives, amylose and pectin, as well as certain natural gums and derivatives thereof, such as gum arabic and salts of alginic acid;

homopoly(amino acid)s having suitable reactive functionalities, such as polylysines, polyhistidines or polyornithines;

natural and synthetic polypeptides and proteins, such as bovine albumin and other mammalian albumins; and synthetic polymers having nucleophilic functional groups, such as polyvinyl alcohols, polyallyl alcohol, polyethylene glycols and substituted polyacrylates.

Very suitable polymers for the purposes of the invention are polysaccharides and derivatives thereof, for example: dextrans, carboxy-methyl-dextrans, hydroxyethyl- and hydroxypropyl-starches, glycogen, agarose derivatives, and hydroxyethyl- and hydroxypropyl-celluloses. As will be apparent from the working examples herein (vide infra), notably dextrans have proved to be particularly suitable polymers in connection with the invention, and they are presently the most preferred polymers.

As already indicated, it is often desirable, particularly for many of the immunochemical applications of reagents and conjugates of the invention, that notably the conjugates of the invention, including conjugates of the invention which are prepared (by a process which also constitutes an aspect of the invention) from reagents of the invention, have no net charge, since the presence of a net positive or negative charge in such cases can lead, inter alia, to undesirable non-specific binding of the conjugates to substances and/or materials other than those of interest. In many cases this condition will, unless charged molecular species are introduced, be fulfilled simply by ensuring that the polymeric carrier itself possesses no net charge; thus, in a further aspect of the invention, the polymeric carrier molecule of a reagent or conjugate of the invention is, in its free state, substantially linear and substantially uncharged at a pH in the range of about 4 to about 10, the latter pH interval being the interval of practical relevance for the vast majority of immunochemical procedures, hybridization procedures and other applications of, notably, conjugates of the invention. Among various polymers which meet this criterion, are, for example, numerous polysaccharides and polysaccharide derivatives, e.g. dextrans and hydroxyethyl- and hydroxypropylcelluloses.

Depending on the use to which a reagent or conjugate of the invention is to be put, reagents and conjugates of the invention may be based on water-soluble polymeric carriers having molecular weights ranging from rather low to very high, and in a further aspect of the invention the polymeric carrier may have a peak molecular weight in the range of about 1,000 to about 40,000,000. Peak molecular weights which are of considerable interest, and which are exemplified in the working examples given herein, are peak molecular weights in the range of about 1,000 to about 80,000, and in the range of about 80,000 to about 2,000,000. A peak molecular weight of particular interest, notably in the case of dextrans as polymeric carriers, is a peak molecular weight of about 500,000.

The term "peak molecular weight" (also denoted "peak average molecular weight") as employed in the present specification and claims in connection with polymeric carriers denotes the molecular weight of greatest abundance, i.e. that molecular weight (among a distribution of molecular weights) which is possessed by the greatest number of molecules in a given sample or batch of the polymer. It is quite normal to characterize numerous types of polymers in this manner, owing to the difficulty (particularly for the highest molecular weights) of obtaining or preparing polymer fractions of very narrow molecular weight distribution. In the case of numerous commercially available polymers which are of interest in the context of the invention, for example dextrans, the manufacturer or distributor will be able to provide reliable peak molecular weight data (determined, for example, by gel-permeation chromatography) which can provide a basis for the selection of a polymer fraction suitable for the preparation of a particular type of reagent or conjugate. It should be mentioned here that peak molecular weight values cited in the present specification and claims refer to the peak molecular weight of the free polymer in question, and take no account of, for example, the possible formation of cross-linked polymer units, e.g. as a result of cross-linking of two or more polymer molecules by reaction with divinyl sulfone during a process according to the invention for the preparation of a reagent or conjugate of the invention; such cross-linked units will, on average, have higher molecular weights than the individual free polymer molecules from which they are formed.

Reagents according to the present invention may clearly be tailored to meet a very wide range of requirements with regard to peak molecular weight of the polymer and the content of free, reactive vinyl groups. A further aspect of the invention relates to reagents based on a polymeric carrier having a peak molecular weight of about 500,000 or about 2,000,000, or having a peak molecular weight in any one of the following ranges:

about 1,000 to about 20,000; about 20,000 to about 80,000; about 80,000 to about 500,000; about 500,000 to about 5,000,000; or about 5,000,000 to about 40,000,000; and having a content of free, reactive vinyl groups in the range of about 1 to about 5,000 µmoles of vinyl groups per gram of polymeric carrier, such as in any of the following sub-ranges (expressed in µmoles of vinyl groups per gram of polymeric carrier):

about 1 to about 50; about 50 to about 300; about 300 to about 1,000; or about 1,000 to about 5,000;

As indicated previously, molecular species in the context of the present invention, i.e. molecular species which are to be attached to a reagent or conjugate according to the invention, or which are already attached to the polymeric carrier of a conjugate of the invention, are to be found among numerous different types of substances, examples being: proteins, such as ferritin, phycoerythrins, phycocyanins or phycobilins; enzymes, such as horseradish peroxidase, alkaline phosphatase, glucose oxidases, galactosidases or ureases; toxins; drugs; dyes; fluorescent, luminescent, phosphorescent or other light-emitting substances; metal-chelating substances, such as iminodiacetic acid, ethylenediaminetetraacetic acid (EDTA), diethylenetriaminepentaacetic acid (DTPA) or desferrioxamine B; substances labelled with a radioactive isotope; or substances labelled with a heavy atom.

In the light of the discussion given earlier, above, it will be clear that the majority of types of substances among these latter examples will be able to serve as labels or markers in conjugates according to the invention. To give some further examples, fluorescent substances may be selected from, e.g., fluorescein (suitably as fluorescein isothiocyanate, FITC), fluoresceinamine, 1-naphthol, 2-naphthol, eosin, erythrosin, morin, o-phenylenediamine, rhodamine and 8-anilino-1-naphthalenesulfonic acid. Radioactive isotopes of relevance may be selected, for example, among isotopes of hydrogen (i.e. tritium, $^3H$), carbon (such as $^{14}C$), phosphorus (such as $^{32}P$), sulfur (such as $^{35}S$), iodine (such as $^{131}I$), bismuth (such as $^{212}Bi$), yttrium (such as $^{90}Y$), technetium (such as $^{99m}Tc$), palladium (such as $^{109}Pd$) and samarium (such as $^{153}Sm$). Heavy atoms of relevance may be selected, for example, among Mn, Fe, Co, Ni, Cu, Zn, Ga, In, Ag, Au, Hg, I, Bi, Y, La, Ce, Eu and Gd. Gold (Au) [possibly in combination with silver (Ag) as an enhancement reagent (vide supra)] is a particularly useful heavy atom in many cases.

In a further aspect of the invention, molecular species in the context of the present invention may also be targetting species [as defined earlier (vide supra)] which are capable of selective binding to, or selective reaction with, a complementary molecule or a complementary structural region of a material of biological origin. Examples of relevant targetting species are, for example: antigens; haptens; monoclonal or polyclonal antibodies; gene probes; natural or synthetic oligo- or polynucleotides; certain natural or synthetic mono-, oligo- or polysaccharides; lectins; avidin or streptavidin; biotin; growth factors; hormones; receptor molecules; or protein A or protein G. For examples of appropriate antibodies, reference is made to the working examples given herein. Examples of relevant hormones may be selected from steroid hormones (e.g. estrogen, progesterone or cortisone), amino acid hormones (e.g. thyroxine) and peptide and protein hormones (e.g. vasopressin, bombesin, gastrin or insulin).

As already made clear, the present invention also relates to a water-soluble conjugate comprising a water-soluble polymeric carrier molecule to which one or more molecular species are covalently attached, each via a linking group derived from divinyl sulfone, the attachment of each of the linking groups to the polymeric carrier molecule being via a covalent linkage formed between one of the two vinyl groups of a divinyl sulfone molecule and a reactive functionality on the carrier molecule, and the attachment of a molecular species to the linking group being via a covalent linkage formed between the other vinyl group originating from the divinyl sulfone molecule and a functional group on the molecular species.

In particularly interesting conjugates of the latter type according to the invention, the polymeric carrier molecule further has covalently attached thereto one or more moieties derived from divinyl sulfone, each of which moieties is attached via a covalent linkage formed between one of the two vinyl groups of a divinyl sulfone molecule and a reactive functionality on the polymeric carrier molecule, at least one such said moiety in its attached state having the remaining vinyl group free and capable of reaction with a further molecular species having a functional group which is reactive towards the free vinyl group.

The attached molecular species in a conjugate of one of the latter types, or of other types (vide infra) according to the invention may suitably be divided up into, for example, molecular species having molecular weights of about 2,000 or below, and molecular species having molecular weights of about 2,000 or above. In the former case, the polymeric carrier molecule of the conjugate may have from 1 to about 10,000 molecular species covalently attached thereto, for example from about 10 to about 1000 molecular species, such as from about 20 to about 500 molecular species covalently attached thereto. In the latter case, i.e. for molecular species of molecular weight about 2,000 or above, the polymeric carrier molecule of the conjugate may have from 1 to about 1000 molecular species covalently attached thereto, for example from 1 to about 500 molecular species, such as from 1 to about 100, from 2 to about 50, or from about 10 to about 50 molecular species covalently attached thereto.

In a further aspect, conjugates of this type according to the invention may be based on a polymeric carrier having a peak molecular weight of about 500,000 or about 2,000,000, or having a peak molecular weight in any one of the following ranges:

about 1,000 to about 20,000; about 20,000 to about 80,000; about 80,000 to about 500,000; about 500,000 to about 5,000,000; or about 5,000,000 to about 40,000,000; and having a sum total content of molecular species and, where relevant, free vinyl groups in the range of about 1 to about 5,000 µmoles of molecular species plus, where relevant, µmoles of vinyl groups per gram of polymeric carrier, such as in any of the following sub-ranges (expressed in µmoles of molecular species plus, where relevant, µmoles of vinyl groups per gram of polymeric carrier):

about 1 to about 50; about 50 to about 300; about 300 to about 1,000; or about 1,000 to about 5,000;

Further molecular species as defined in the context of the invention may have any of the characteristics mentioned previously, above, in connection with molecular species.

Yet another aspect of the invention relates to a water-soluble conjugate comprising a water-soluble polymeric carrier molecule to which are covalently attached two or more molecular species, at least one of which is different from the other(s), each molecular species being attached via a linking group derived from divinyl sulfone, the attachment of each linking group to the polymeric carrier molecule being via a covalent linkage formed between one of the two vinyl groups of a divinyl sulfone molecule and a reactive functionality on said carrier molecule, and the attachment of a molecular species to the linking group being via a covalent linkage formed between the other vinyl group originating from the divinyl sulfone molecule and a functional group on the molecular species.

Conjugates of this latter type according to the invention may be based on a polymeric carrier having a peak molecular weight of about 500,000 or about 2,000,000, or having a peak molecular weight in any one of the following ranges:

about 1,000 to about 20,000; about 20,000 to about 80,000; about 80,000 to about 500,000; about 500,000 to about 5,000,000; or about 5,000,000 to about 40,000,000; and having a total content of covalently attached molecular species in the range of about 1 to about 5,000 µmoles of molecular species per gram of polymeric carrier, such as in any of the following sub-ranges (expressed in µmoles of molecular species per gram of polymeric carrier):

about 1 to about 50; about 50 to about 300; about 300 to about 1,000; or about 1,000 to about 5,000;

As already indicated, the invention also relates to methods of preparation of a reagent or conjugate according to the invention: thus, in one such aspect the invention provides a method for the preparation of a water-soluble reagent according to the invention, i.e. a water-soluble reagent comprising a water-soluble polymeric carrier molecule having covalently attached thereto one or more moieties derived from divinyl sulfone, each of which moieties is attached via a linkage formed between one of the two vinyl groups of a divinyl sulfone molecule and a reactive functionality on the polymeric carrier molecule, at least one such moiety in its attached state having the remaining vinyl group free and capable of reaction with a molecular species having a functional group which is reactive towards the free vinyl group.

The method in question according to the invention comprises allowing the water-soluble polymeric carrier to react with divinyl sulfone in aqueous solution at a pH above 5. In its most general form, the reaction may take place at a temperature in the range of 0°–60° C., although a temperature in the range of 20°–25° C. will often be quite suitable, as illustrated, for example, for polymeric carriers such as dextrans and certain polysaccharide derivatives in the working examples given herein. The pH at which the reaction takes place is generally within the range of about 10–11.5, which is a pH range in which divinyl sulfone is particularly reactive towards reactive functionalities on most types of polymeric carriers.

As far as the concentration of the polymeric carrier in the aqueous solution is concerned, it will generally be within the range of 0.1–20% w/v, and often in the range of 1–10% w/v. The concentration of divinyl sulfone in the aqueous solution will generally be in the range of 0.1–15% v/v, and often in the range of 1–10% v/v.

It is difficult to give general guidelines concerning the period of time for which the reaction of divinyl sulfone with the polymeric carrier in aqueous solution should be allowed to proceed, since these will vary rather considerably, depending, e.g., the temperature and pH at which the reaction occurs, the concentration of the polymeric carrier and of divinyl sulfone in the reaction mixture, the nature and/or molecular weight of the polymeric carrier, and the extent to which cross-linking of the polymeric carrier (by reaction with divinyl sulfone) may proceed before there is a risk, for example, of gelling or precipitation taking place; as is clearly illustrated in the working examples herein in the case of dextrans, the reaction time may be an important factor for at least some classes of polymeric carriers. The reaction time in question will, however, normally be within the range of 5–120 minutes.

As also indicated previously, the present invention also provides a method for the preparation of a water-soluble conjugate according to the invention based on a water-soluble polymeric carrier molecule to which one or more molecular species are covalently attached, each via a linking group derived from divinyl sulfone, the attachment of each of the linking groups to the polymeric carrier molecule being via a covalent linkage formed between one of the two vinyl groups of a divinyl sulfone molecule and a reactive functionality on the carrier molecule, and the attachment of a molecular species to the linking group being via a covalent linkage formed between the other vinyl group originating from the divinyl sulfone molecule and a functional group on the molecular species; the same method also applies to the preparation of such conjugates in which the polymeric carrier molecules further have covalently attached thereto one or more reactive moieties derived from divinyl sulfone.

The method in question comprises:

allowing the water-soluble polymeric carrier to react with divinyl sulfone in aqueous solution at a pH above 5, so as to form an aqueous solution containing a water-soluble intermediate reagent comprising molecules of the water-soluble polymeric carrier having covalently attached thereto one or more reactive moieties derived from divinyl sulfone, optionally subjecting the water-soluble intermediate reagent to a purification step, and allowing the optionally purified water-soluble intermediate reagent to react, via its reactive moieties, with a molecular species in aqueous solution at a pH above 5.

The optional purification step may, for example, involve a process such as dialysis (for the removal of unwanted salts or other species of low molecular weight) or gel chromatography. The pH and temperature conditions, and the concentrations of polymeric carrier and divinyl sulfone during the reaction of the polymeric carrier with divinyl sulfone will generally be as described previously in connection with the preparation of water-soluble reagents of the invention, and the comments made concerning reaction time are also relevant here.

As regards the reaction of the water-soluble intermediate reagent with the molecular species in the final stage of the process, the temperature during the reaction will generally be in the range of 0°–60° C., and often in the range of 20°–25° C. The concentration of molecular species in the aqueous reaction medium will generally be in in the range of 0.1–20% v/v, and the pH of the solution will generally be in the range of about 8–12.

In a particularly interesting aspect of the latter method of the invention, the aqueous solution in which the molecular species reacts with the optionally purified water-soluble intermediate reagent contains a lyotropic salt, i.e. a salt which has the property, e.g., of promoting the precipitation ("salting-out") of certain types of high molecular weight species, in particular proteins, from aqueous solution. The effectiveness (demonstrated in the working examples herein) of the incorporation of such a lyotropic salt in enhancing the attachment of molecular species to the reactive vinyl groups present in the water-soluble intermediate reagent formed during the process of the invention is contemplated to derive from the "salting-out" effect mentioned above.

Suitable lyotropic salts may be selected among sulfates, phosphates, citrates and tartrates of lithium, sodium, potassium and ammonium, and the lyotropic salt will normally be present in a concentration corresponding to an ionic strength of at least 0.01, for example a concentration corresponding to an ionic strength of at least 0.3. A suitable concentration will often be a concentration corresponding to an ionic strength in the range of 0.5–5.

As already indicated above, the influence of lyotropic salts in methods of the invention is particularly noteworthy in the case of molecular species which are proteins or polypeptides.

It will be apparent that reagents of the invention correspond in composition to the water-soluble intermediate reagents formed in the course of the latter method; thus, yet another aspect of the invention relates to a method for the preparation of the same type of water-soluble conjugate as in the preceding method, the method comprising allowing a water-soluble reagent according to the invention to react with a molecular species in aqueous solution at a pH above 5. The nature of the molecular species involved, and the conditions applying in the process (including the influence of lyotropic salts) are generally as already described, above.

A still further aspect of the invention relates to a method for the preparation of a water-soluble conjugate according to the invention, which conjugate comprises a water-soluble polymeric carrier molecule to which are covalently attached two or more molecular species, at least one of which is different from the other(s), each molecular species being attached via a linking group derived from divinyl sulfone, the attachment of each linking group to the polymeric carrier molecule being via a covalent linkage formed between one of the two vinyl groups of a divinyl sulfone molecule and a reactive functionality on the carrier molecule, and the attachment of a molecular species to said linking group being via a covalent linkage formed between the other vinyl group originating from said divinyl sulfone molecule and a functional group on said molecular species.

The method in question comprises:

(i) allowing the water-soluble polymeric carrier to react with divinyl sulfone in aqueous solution at a pH above 5, so as to form an aqueous solution containing a water-soluble intermediate reagent comprising molecules of the water-soluble polymeric carrier having covalently attached thereto two or more reactive moieties derived from divinyl sulfone, (ii) optionally subjecting the water-soluble intermediate reagent to a purification step, (iii) allowing the optionally purified water-soluble intermediate reagent to react, via its reactive moieties, with a molecular species in aqueous solution at a pH above 5 so as to form a water-soluble intermediate conjugate, the conditions being such that not all of the reactive moieties react with a molecular species, (iv) optionally subjecting the water-soluble intermediate conjugate to a purification step, and (v) allowing the optionally purified water-soluble intermediate conjugate to react, via previously unreacted reactive moieties, with a further molecular species in aqueous solution at a pH above 5, the further molecular species being different from that already attached in the intermediate conjugate.

The concentrations of the various components, as well as the conditions prevailing in the reaction steps, will generally be as already described. The concentration of further molecular species, and the other conditions associated with the reaction thereof, will generally be as for molecular species. As before, the inclusion of a lyotropic salt in the reactiom media for reaction of the molecular species and the further molecular species (particularly when these are proteins or polypeptides) is a preferred aspect.

In a further aspect of this method, any remaining free vinyl groups present in the conjugate formed in step (v) are deactivated, the deactivation being achieved by the addition, to the aqueous solution of the conjugate, of an excess of a deactivating species of low molecular weight; suitable deactivating species may be, for example, ethanolamine, mercaptoethanol, or certain amino acids, e.g. cysteine, glycine, alanine or valine.

It will be apparent that those conjugates of the invention which have a molecular species attached and further have reactive vinyl groups correspond in composition to the water-soluble intermediate conjugates formed in the course of the latter method; thus, yet another aspect of the invention relates to a method for the preparation of the same type of water-soluble conjugate as in the preceding method, the method comprising allowing a water-soluble conjugate of the mentioned type according to the invention to react with a further molecular species in aqueous solution at a pH above 5, the further molecular species being different from that already attached in the reacting conjugate.

The conditions pertaining to the reaction, as well as the nature of the further molecular species, will generally be as already described above in connection with the preceding method of the invention.

The invention also relates to products (reagents and conjugates) produced by the various methods of the invention. The invention further relates to the use of such conjugates, and of other conjugates of the invention, in procedures or techniques involving the interaction of a target moiety or target functionality (e.g. an antigen-binding site of an antibody) with a targetting species as defined herein.

More particularly, the invention relates to the use of conjugates produced by the various methods of the invention, and of other conjugates of the invention, in procedures or techniques of the following types: immunochemical assay techniques, including enzymatic immunoassays (EIA) such as ELISA, radioimmunoassays (RIA), and nephelometric and turbidimetric immunoassays; immunohistochemical procedures; cytochemical procedures; flow cytometry; in situ hybridization techniques; membrane hybridization techniques (i.e. techniques in which a hybridization reaction takes place on a membrane or sheet, such as a nitrocellulose membrane or sheet), including Southern and northern blotting; and methods based on lectin/carbohydrate interactions. The use of such conjugates in biosensors or biosensor systems is also within the scope of the present invention.

Examples of techniques or procedures in which conjugates of—or produced according to—the invention are particularly useful are: detection of antigenic determinants or antibodies in tissues or in/on cells using immunohistochemical/cytochemical procedures; "amplification" of the sensitivity of detection for such immunochemical reactions; detection of antigenic determinants, haptens or antibodies in a sample using immunoassays or immunoblotting procedures; "amplification" of the sensitivity of detection in such immunoassays or immunoblotting procedures; detection of target nucleic acid sequences via hybridization reactions; and "amplification" of the sensitivity of detection of such hybridization reactions.

BRIEF DESCRIPTION OF THE DRAWINGS

The invention is illustrated in greater detail by the following Examples, with reference to the appended drawings which are as follows.

ABBREVIATIONS

Figure 1:
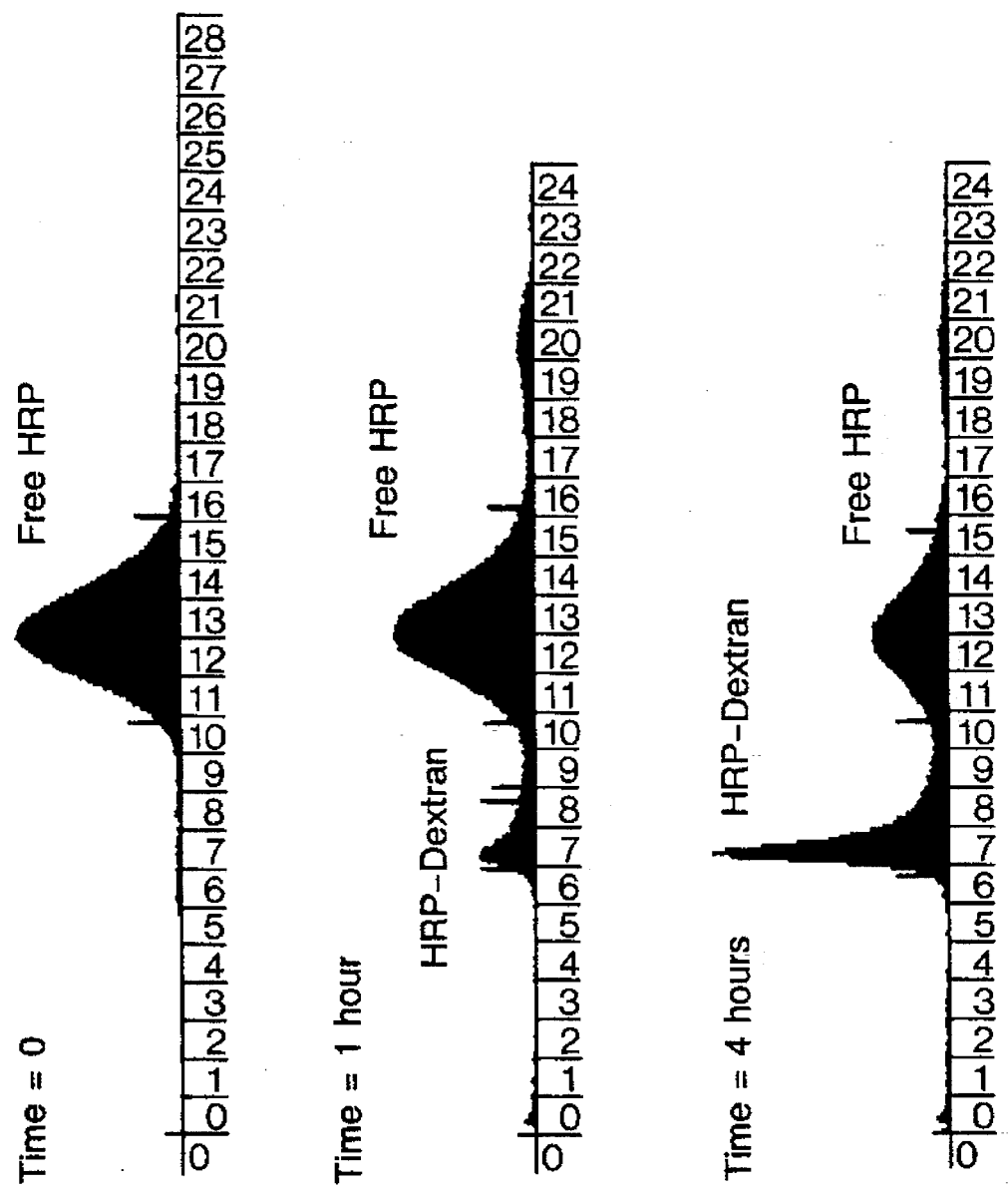
FIG. 1: Results from Example 11. Gel-filtration UV-absorption profiles for samples from coupling of horseradish peroxidase (HRP) to DVS-activated dextran of peak MW 500,000. The profiles for free and dextran-bound HRP are shown for samples subjected to coupling times of 0, 1 hour and 4 hours, respectively (gel-filtration performed on Sephacryl™ S-200). Horizontal axis: elution volume in ml.

The following abbreviations are employed in the Examples given below and elsewhere in the specification:
BSA: bovine serum albumin
DVS: divinyl sulfone
MW: molecular weight
HRP: horseradish peroxidase
FITC: fluoresceinisothiocyanate
PSA: prostate-specific antigen
GAM: goat anti mouse Ig
RAM: rabbit anti mouse Ig
AP: alkaline phosphatase
SPDP: N-succinimidyl 3-(2-pyridyldithio)propionate
DTT: dithiothreitol
LSAB: labelled streptavidin biotin
cat.: catalogue
Fab: fragment antigen binding Unless indicated otherwise, the water employed in the following examples was water from a Milli Q™ apparatus, i.e. water which had been subjected to filtration through a Millipore™ filter and subsequent deionization.

GENERAL DESCRIPTION OF DETECTION/ASSAY PROCEDURES EMPLOYED

A general outline of immunohistochemical and cytochemical detection is given in the introductory part of the present specification, and such detection procedures can be carried out by a skilled person using established, readily available methods.

Detection of target nucleic acid sequences using labelled probes is also outlined in the introductory part of the present specification, and can similarly be carried out by a skilled person using established, readily available procedures. In the context of the present invention, "amplification" (i.e. increase in the detection sensitivity) in connection with detection of the occurrence of a hybridization reaction can be achieved by using, for example, a biotin-labelled probe for the hybridization and a conjugate according to the invention comprising, e.g., anti biotin antibodies, avidin or streptavidin as reagent for detection of the hybridization.

General ELISA procedure: As also outlined in the introductory part of the present specification, an important class of immunoassay procedures are the so-called ELISA procedures. In the working examples herein (vide infra), the ELISA procedures are performed using three "layers" or—in certain special cases—two layers as follows:

Three layers: After adsorption of antibody ("catching antibody") to the wells of a polystyrene microtiter plate (NUNC, Denmark) (giving the 1st layer), the complementary antigen or biotin-conjugated antigen is bound as a 2nd layer. The 3rd layer in the form of a conjugate according to the invention comprising enzyme (horseradish peroxidase) and either (i) an antigen-specific antibody, or (ii) (when the complementary antigen in the 2nd layer is labelled with biotin) avidin or streptavidin is then introduced. Finally, the bound, enzyme-labelled conjugate is then detected by adding a colour-development reagent (ortho-phenylenediamine/ hydrogen peroxide) which is a substrate for the enzyme. Appropriate washing is performed between these various steps (vide infra).

Two layers: The appropriate antigen or biotin-labelled antigen is adsorbed directly to the inner surface of microtiter plate wells, i.e. the catching antibody is omitted.

In Examples 37B, 37C and 38 (vide infra), three layers are used as described above, with the following details:

1st layer: 100 μ of goat anti rabbit Ig dilution in each well. Incubation overnight at +4° C.

Blocking of remaining binding sites: 200 μl of 0.1M dipotassium hydrogen phosphate, 1% Tween™ 20, pH 7.2.

Incubation: 30 minutes at room temperature.

Washing procedure: The microtiter plate wells are emptied by inverting the plate and "flicking" it over a sink. Residual liquid is removed by further tapping the inverted microtiter plate against filter paper. The wells are then filled with 0.1M dipotassium hydrogen phosphate, 0.5M NaCl, 0.1% Tween™, pH 7.2, and the plate is gently rocked for 3–5 minutes. This procedure is repeated twice.

2nd layer: 100 μl of rabbit IgG (1 ng/ml) or (when the 3rd layer is to comprise a streptavidin conjugate) 100 μl of biotin-conjugated rabbit IgG (0.1 ng/ml) in each well. [Control: 100 μl of dilution buffer (see the Examples in question)]. Incubation overnight at +4° C. Washing as described above under "Washing procedure".

3rd layer: 100 μl of HRP-dextran/goat anti rabbit Ig dilution or 100 μl of HRP-dextran/streptavidin conjugate preparation in each well. The plate is gently rocked for 2 h. Washing as described in "washing procedure". 100 μl of colour-development reagent solution is added, followed after 15 minutes by addition of 100 μl of 1M $H_2SO_4$. The colour intensity in the individual wells is then measured using an automatic ELISA reader.

In Example 40 (vide infra), two layers are used as described above, with the following details:

1st layer: 100 μl of biotin-conjugated rabbit IgG dilution in each well. Incubation overnight at +4° C.

Blocking of remaining binding sites: 200 μl of 0.1M dipotassium hydrogen phosphate, 1% Tween™ 20, pH 7.2. Incubation for 30 minutes at room temperature. Washing as described above under "Washing procedure".

2nd layer: 100 μl of HRP-dextran/streptavidin preparation or 100 μl of conventional streptavidin-peroxidase conjugate in each well. 100 μl of colour-development reagent solution is added, followed after 15 minutes by addition of 100 μl of 1M $H_2SO_4$. The colour intensity in the individual wells is then measured using an automatic ELISA reader.

In Examples 56, 57 and 58 (vide infra), two layers are used as described above, with the following details:

1st layer: 100 μl of normal human serum dilution in each ELISA-well. Incubation overnight at +4° C.

Washing procedure: The wells of the microtiter plate are emptied and washed (5×1 minute) using an automatic wellwasher (Denley, well-wash- 4). The washing buffer is: 0.01M sodium phosphate, 0.145M NaCl, 0.1% Tween™ 20, pH 7.2.

2nd layer: In each well either 100 μl of HRP-dextran/ RAM conjugate complexed with mouse anti human kappa light chains dilution, or 100 μl of HRP-dextran/streptavidin conjugate complexed with biotinylated mouse anti human kappa light chains dilution. Incubation with gentle shaking for 1.5 hours at approx. 20° C. Washing as described above. 100 μl of colour-development reagent solution is added, followed after 10 minutes (in Examples 56 and 58) or after 2 minutes (in Example 57) by addition of 100 μl of 1M $H_2SO_4$. The colour intensity in the individual wells is then measured using an automatic ELISA reader.

General procedure for Dot Blot (immunoblotting): The general procedure for immunoblotting [as employed in Examples 37C and 40 herein (vide infra)] is as follows:

Antigen or biotin-conjugated (biotinylated) antigen is immobilized on nitrocellulose membranes in the form of dots of a serial dilution. After blocking of remaining binding sites, the nitrocellulose membranes are incubated with the appropriate peroxidase-containing conjugate with binding specificity for the (optionally biotinylated) antigen.

After washing, colour-development reagent (diaminobenzidine/hydrogen peroxide) is added, the intensity of the colour generated being proportional to the amount of enzyme present in the form of conjugate bound to the (optionally biotinylated) antigen in the dots.

Procedure: 1 μl of (optionally biotinylated) rabbit IgG at dilutions of 6, 3, 1.5, 0.75, 0.38, 0.19, 0.10, 0.05 and 0.025 ng/μl is applied to the nitrocellulose membrane; the dilution medium is 0.1M NaCl containing 50 mg of BSA/1000 ml.

Blocking of remaining binding sites: 0.1M potassium phosphate, 1% Tween™, pH 7.2, for 2 minutes.

General washing procedure: the nitrocellulose membrane is washed in 0.1M dipotassium hydrogen phosphate, 0.5M NaCl, 0.1% Tween™, pH 7.2, for 5 minutes with gently rocking; the spent washing buffer is then removed. The procedure is repeated twice.

The conjugate to be tested is diluted in 0.1M potassium phosphate, 1% BSA, 0.1% Tween™, pH 7.2. Washing as described above under "General washing procedure". The membrane is immersed in the colour-development reagent, and after 15 minutes the membrane is then washed once with distilled water. The lowest dilution of antigen giving a positive dot is determined.

EXAMPLE 1

Divinyl sulfone activation of hydroxyethyl-cellulose

One gram of hydroxyethyl-cellulose ("Natrosol 250 HR", Aqualon, Germany) was dissolved in 50 ml of water at room temperature (20°–25° C.), and to the solution was added 50 ml of 0.5M dipotassium hydrogen phosphate/sodium hydroxide (pH 11.5) and 25 mg of sodium borohydride. Immediately after dissolution of the sodium borohydride, the reaction mixture was transferred to a well ventilated hood and 5 ml of divinyl sulfone (Aldrich, cat. No. V370, 97% pure) was added. Gentle stirring was performed with a magnetic stirrer. After 10 and 30 minutes, respectively, 50 ml aliquots of the solution were withdrawn. The pH of each aliquot was adjusted to 6–7 with 5M hydrochloric acid (to quench the reaction). Each of the two solutions was then dialysed against 4×5 l of water over a period of two days at room temperature. After dialysis the volume of each solution had increased to 76 ml, corresponding to a final concentration of DVS-activated hydroxyethyl-cellulose of 6.6 mg/ml.

The content of free, reactive vinyl groups (i.e. "dangling" terminal vinyl groups of DVS-derived moieties which are covalently attached to the polymer substrate via a linkage formed by reaction of one of the two vinyl groups of DVS with, in this case, a hydroxy group on hydroxyethyl-cellulose) was determined by reaction with a large excess of sodium thiosulfate followed by titration of the resulting hydroxide ions with standard hydrochloric acid. The reaction of the free vinyl groups with thiosulfate ion takes place according to the following reaction scheme [Porath et al., *J. Chromatogr.* 103 (1975) 49]:

(SUBSTRATE)—O—CH$_2$—CH$_2$—SO$_2$—CH=CH$_2$+S$_2$O$_3^-$+ H$_2$O→

(SUBSTRATE)—O—CH$_2$—CH$_2$—SO$_2$—CH$_2$—CH$_2$—S$_2$O$_3^-$+ OH[31]

The titration results indicated that the samples of DVS-activated hydroxyethyl-cellulose had a content of 150 and 818 μmoles of vinyl groups per gram of hydroxyethyl-cellulose after 10 and 30 minutes of activation, respectively.

EXAMPLE 2

Divinyl sulfone activation of hydroxypropyl-starch

A reaction and dialysis procedure exactly analogous to that described in Example 1 was employed, starting with 1 gram of hydroxypropyl-starch ("Reppal PES 200", Reppe Glykos AB, Sweden). After dialysis, the volume of the solution derived from the aliquot withdrawn after 10 minutes had increased to 64 ml, whilst that of the solution derived from the aliquot withdrawn after 30 minutes had increased to 78 ml. This corresponds to a final concentration of DVS-activated hydroxypropyl-starch of 7.8 and 6.4 mg/ml, respectively.

Using the titration procedure described in Example 1, the content of reactive vinyl groups in the two samples of DVS-activated hydroxypropyl-starch was determined to be 1026 and 2568 μmoles of vinyl groups per gram of hydroxypropyl-starch, respectively.

Upon carrying out an analogous activation procedure at a pH of 11.5 instead of 11.0, extensive gelling and precipitation of the activated product occurred.

EXAMPLE 3

Divinyl sulfone activation of bovine serum albumin

Two grams of bovine serum albumin (98% pure, Sigma Chemical Company) was dissolved in 200 ml of 0.25M dipotassium hydrogen phosphate/sodium hydroxide (pH 10.0) at room temperature (20°–25° C.). 2 ml of divinyl sulfone was added (HOOD!). Gentle stirring was performed with a magnetic stirrer. After 60 minutes the pH of the reaction mixture was adjusted to 6–7 with 5M hydrochloric acid. The solution was then dialysed against 4×5 l of 0.1M sodium chloride over a period of two days at room temperature.

After dialysis the volume of the solution had increased to 215 ml, corresponding to a final concentration of DVS-activated BSA of 9.3 mg/ml.

Using the previously described procedure, the content of reactive vinyl groups was determined to be 184 μmoles per gram of BSA, corresponding to ca. 12 moles of vinyl groups per mole of BSA.

EXAMPLE 4

Divinyl sulfone activation of dextran (peak PEW 500,000). The influence of DVS concentration Five separate solutions (A-E) containing uniform concentrations of dextran with a peak molecular weight of 500,000 (Pharmacia, Sweden) and different concentrations of DVS were prepared so as to give the following final concentrations:

All solutions: 5% w/v of dextran; 0.25M dipotassium hydrogen phosphate/sodium hydroxide (pH 11.5); 0.25 mg of sodium borohydride per ml, DVS concentrations:
solution A: 10% v/v
solution B: 5% v/v
solution C: 3% v/v
solution D: 1% v/v
solution E: 0.5% v/v The activation was performed at 25° C. for 15 minutes. After activation, the pH of the reaction mixtures was adjusted to 7 with 5M hydrochloric acid. All samples were dialysed thoroughly against water to remove excess reagents.

The content of reactive vinyl groups for the various samples of DVS-activated dextran was determined as described in Example 1. The results (see the table below) may be expressed as μmoles of vinyl groups per gram of dextran; they may alternatively, based on the assumption of an average molecular weight of 500,000 (as further discussed in the text), be given as moles of vinyl groups per mole of dextran:

| Solution | μmoles vinyl groups/ g dextran | moles vinyl groups/ mole dextran |
| --- | --- | --- |
| A | 542 | 271 |
| B | 414 | 207 |
| C | 234 | 117 |
| D | 179 | 89.5 |
| E | 86 | 43 |

EXAMPLE 5

Divinyl sulfone activation of dextran (peak MW 500,000). The influence of DVS concentration at high dextran concentration Four separate solutions (A–D) containing uniform concentrations (twice as great as in Example 4) of dextran with a peak molecular weight of 500,000 (Pharmacia, Sweden) and different concentrations of DVS were prepared so as to give the following final concentrations:

All solutions: 10% w/v of dextran; 0.25M dipotassium hydrogen phosphate/sodium hydroxide (pH 11.5); 0.25 mg of sodium borohydride per ml, DVS concentrations:
solution A: 10% v/v
solution B: 5% v/v
solution C: 3% v/v
solution D: 1% v/v The activation was performed at 25° C. for 15 minutes. After activation, the pH of the reaction mixtures was adjusted to 7 with 5M hydrochloric acid. All samples were dialysed thoroughly against water to remove excess reagents.

The content of reactive vinyl groups for the various samples of DVS-activated dextran was determined as described in Example 1. The results are summarized below:

| Solution | μmoles vinyl groups/ g dextran | moles vinyl groups/ mole dextran |
|---|---|---|
| A | 944 | 472 |
| B | 583 | 292 |
| C | 335 | 168 |
| D | 194 | 97 |

EXAMPLE 6

Divinyl sulfone activation of dextran (peak MW 500,000). The influence of time at low dextran concentration Four separate solutions (A-D) containing uniform, low concentrations of dextran with a peak molecular weight of 500,000 (Pharmacia, Sweden) and DVS were prepared so as to give the following final concentrations:

All solutions: 1% w/v of dextran; 0.25M dipotassium hydrogen phosphate/sodium hydroxide (pH 11.5); 0.25 mg of sodium borohydride per ml, DVS concentrations:
solution A: 5% v/v
solution B: 5% v/v
solution C: 10% v/v
solution D: 10% v/v For solutions A and C, activation was allowed to proceed for 30 minutes. In the case of solutions B and D, activation was allowed to proceed for 60 minutes. The activation was performed at 25° C., and after activation the pH of each solution was adjusted to 7 with 5M hydrochloric acid.

Results: With solution B, precipitation of a solid gel occurred in the activation vessel after 50 minutes of reaction. With solution D, precipitation of a solid gel occurred after 40 minutes of reaction. The reaction mixtures from these two solutions were therefore discarded.

The solutions obtained with A and C were dialysed thoroughly against water to remove excess reagents.

The content of reactive vinyl groups for the two samples of DVS-activated dextran was determined as described in Example 1. The results are summarized below:

| Solution | μmoles vinyl groups/ g dextran | moles vinyl groups/ mole dextran |
|---|---|---|
| A | 1500 | 750 |
| C | 2760 | 1380 |

EXAMPLE 7

Divinyl sulfone activation of dextrans with different peak molecular weights between 100,000 and 500,000

Four dextrans (Pharmacosmos, Denmark; designated here as D1–D4) with different specified peak molecular weights (see below) were activated with divinyl sulfone under uniform conditions.

| Dextran | Peak MW of dextran |
|---|---|
| D1 | 123,600 |
| D2 | 196,300 |
| D3 | 276,500 |
| D4 | 401,300 |

Conditions for DVS activation: 5% w/v of the appropriate dextran; 0.25M dipotassium hydrogen phosphate/sodium hydroxide (pH 11.5); 0.25 mg of sodium borohydride per ml; 5% v/v of divinyl sulfone.

Activation was performed at room temperature for 15 minutes. The pH of each reaction mixture was then adjusted to 7 with 5M hydrochloric acid, after which the samples were dialyzed thoroughly against water.

The content of reactive vinyl groups in the samples of DVS-activated dextrans was determined as described in Example 1. The results are summarized below:

| Solution | μmoles vinyl groups/ g dextran | moles vinyl groups/ mole dextran |
|---|---|---|
| D1 | 861 | 106 |
| D2 | 735 | 144 |
| D3 | 780 | 216 |
| D4 | 734 | 295 |

EXAMPLE 8

Divinyl sulfone activation of dextran with peak MW 2,000,000

One gram of dextran with peak MW 2,000,000 (Pharmacia, Sweden) was dissolved in 50 ml of water at room temperature (20°–25° C.), and to the solution was added 50 ml of 0.5M dipotassium hydrogen phosphate/sodium hydroxide (pH 11.5) and 25 mg of sodium borohydride. 1 ml of divinyl sulfone was added and the mixture was stirred gently with a magnetic stirrer for 30 minutes. The pH of the reaction mixture was then adjusted to 6–7 with 5M hydrochloric acid, after which the solution was dialyzed against 4×5 l of water over a period of two days at room temperature.

The content of reactive vinyl groups was determined, using the titration procedure described in Example 1, to be 567 μmoles per gram of dextran, corresponding to 1134 moles of vinyl groups per mole of dextran having an average MW of 2,000,000.

EXAMPLE 9

Divinyl sulfone activation of dextran with peak MW 20,000

50 grams of dextran with peak MW 20,000 (Sigma Chemical Company) was dissolved in 450 ml of water at room temperature (20°–25° C.), and to the solution was added 450 ml of 0.5M dipotassium hydrogen phosphate/ sodium hydroxide (pH 11.5) and 250 mg of sodium borohydride. 100 ml of divinyl sulfone was added and the mixture was stirred gently with a magnetic stirrer for 15 minutes. The pH of the reaction mixture was then adjusted to 6–7 with 5M hydrochloric acid, after which the solution was dialyzed against water to remove excess reagents.

The content of reactive vinyl groups was determined, using the titration procedure described in Example 1, to be 1230 μmoles per gram of dextran, corresponding to about 25 moles of vinyl groups per mole of dextran having an average MW of 20,000.

EXAMPLE 10

Stability of DVS-activated dextran

Dextran with a peak MW of 500,000 (Pharmacia, Sweden) was activated with divinyl sulfone as described for solution B in Example 4 (i.e. using 5% w/v of dextran and 5% v/v of DVS). The resulting DVS-activated dextran was found to contain 475 μmoles of vinyl groups per gram of dextran.

To the activated dextran solution (35 mg of dextran per ml) was added 0.01% w/v of 1,1,1-trichloro-2-methyl-2-propanol (Sigma, cat. No. T 5138) as a preservative, and four samples of the resulting solution were incubated in the dark in sealed containers at different temperatures as follows:

| Solution sample | Temperature (°C.) |
| --- | --- |
| A | −20 |
| B | 4 |
| C | 20 |
| D | 30 |

The content of reactive vinyl groups was determined after 3 months of incubation, and the results are summarized below:

| Solution sample | μmoles vinyl groups/g dextran |
| --- | --- |
| A | 420 |
| B | 415 |
| C | 415 |
| D | 405 |

It is apparent that the content of reactive vinyl groups has not decreased appreciably after 3 months, and that this remarkable stability persists even at temperatures as relatively high as 30° C.

EXAMPLE 11

Covalent coupling of horseradish peroxidase to DVS-activated dextran (peak MW 500,000) at high temperature Dextran of peak MW 500,000 was activated with DVS as described for "Solution B" in Example 4 (i.e. using 5% w/v of dextran and 5% v/v of DVS). The activated dextran had a content of 490 μmoles of reactive vinyl groups per gram of dextran. The final concentration of DVS-activated dextran was 26 mg/ml. This batch of DVS-activated dextran solution is hereafter referred to as "batch Dex-I".

The procedure for coupling horseradish peroxidase was as follows: 3 ml of DVS-activated dextran solution ("batch Dex-I") were mixed with a solution of 300 mg of horseradish peroxidase (Kem-En-Tec, Copenhagen, Denmark) in 12 ml of water. To the mixture was then added 15 ml of 0.4M dipotassium hydrogen phosphate/sodium hydroxide (pH 10.4). The clear solution was incubated at 37° C. without stirring.

Samples were withdrawn after various periods of time, and the coupling efficiency, i.e. percentage of the originally added horseradish peroxidase coupled to the activated dextran, was determined by gel filtration on Sephacryl™ S-200 (Pharmacia, Sweden). The coupling reaction was stopped after 4 hours of incubation by lowering the pH to 7 by addition of 1M hydrochloric acid.

The coupling results are summarized in FIG. 1. From the relative areas of the peaks, the following coupling efficiencies as a function of incubation time were determined:

| Incubation time (hours) | Coupling efficiency (%) |
| --- | --- |
| 1 | 12 |
| 2 | 25 |
| 3 | 39 |
| 4 | 50 |

These results may be recalculated to give the average number of peroxidase molecules coupled to the dextran, assuming an average molecular weight of 500,000 for the dextran and 40,000 for the peroxidase (as further discussed in the text):

| Incubation time (hours) | moles HRP/mole dextran |
| --- | --- |
| 1 | 5.8 |
| 2 | 12 |
| 3 | 19 |
| 4 | 24 |

EXAMPLE 12

Covalent coupling of horseradish peroxidase to DVS-activated dextran (peak MW 500,000) at low temperature The coupling procedure was as follows: 3 ml (containing 78 mg of DVS-activated dextran in solution) of "batch Dex-I" (see Example 11) were mixed with a solution of 300 mg of horseradish peroxidase (Kem-En-Tec, Copenhagen, Denmark) in 12 ml of water. To the mixture was then added 15 ml of 0.4M dipotassium hydrogen phosphate/sodium hydroxide (pH 10.4). The clear solution was incubated at 4° C. without stirring. Samples were withdrawn after various periods of time, and the coupling efficiency was determined by gel filtration on Sephacryl™ S-200 (Pharmacia, Sweden) in the same way as described in Example 11. The coupling reaction was stopped after 192 hours of incubation by lowering the pH to 7 by addition of 1M hydrochloric acid. The coupling results were as follows:

| Incubation time (hours) | Coupling efficiency (%) | moles HRP/mole dextran |
| --- | --- | --- |
| 5 | 14 | 6.7 |
| 24 | 24 | 12 |
| 48 | 34 | 16 |
| 192 | 40 | 19 |

EXAMPLE 13

Covalent coupling of horseradish peroxidase to DVS-activated dextrans with different degrees of activation Horseradish peroxidase was coupled to the seven DVS-activated dextran preparations produced as described in Examples 4 and 6 (i.e. A–E of Example 4, and A and C of Example 6). The coupling procedure was as follows:

All seven dextran preparations were mixed with horseradish peroxidase and buffer to give the following final concentrations: 2.75 mg of DVS-activated dextran per ml; 10 mg horseradish peroxidase per ml; 0.2M dipotassium hydrogen phosphate/sodium hydroxide (pH 10.0).

Coupling was performed at 37° C. for 16 hours, after which the reaction was stopped by adjusting the pH of the solution to 6–7 by addition of 1M hydrochloric acid. Coupling efficiency was determined by gel filtration on Sephacryl™ S-200 (Pharmacia, Sweden) in the same way as described in Example 11, and the results were as follows:

| µmoles vinyl groups/ g dextran | Coupling efficiency (%) | moles HRP/mole dextran |
| --- | --- | --- |
| 2760 | 71 | 32 |
| 1500 | 62 | 28 |
| 542 | 48 | 22 |
| 414 | 40 | 18 |
| 234 | 26 | 12 |
| 179 | 19 | 8.6 |
| 86 | 15 | 6.8 |

EXAMPLE 14

Covalent coupling of horseradish peroxidase to DVS-activated dextrans with peak MW's between 100,000 and 2,000,000

Five dextrans (Pharmacosmos, Denmark) with different peak MW's between 100,000 and 2,000,000 and activated with divinyl sulfone according to Examples 7 and 8 were coupled with horseradish peroxidase.

The procedure for coupling horseradish peroxidase was as follows:

400 mg of horseradish peroxidase (Kem-En-Tec, Copenhagen, Denmark) and 100 mg of DVS-activated dextran were dissolved in buffer to give the following final concentrations:

10 mg of horseradish peroxidase/ml;
2.5 mg of DVS-activated dextran/ml;
0.2M dipotassium hydrogen phosphate/sodium hydroxide (pH 10.6).

Incubation was performed at 4° C. for 48 hours, followed by gel filtration on Sephacryl™ S-200 to determine the amount of peroxidase coupled to the dextrans. The results are expressed as the average number of horseradish peroxidase molecules attached to one molecule of dextran with an average MW corresponding to the peak MW of the dextran (mole HRP/mole dextran):

| | peak MW of dextran | coupling yield moles HRP/mole dextran |
| --- | --- | --- |
| A | 123,600 | 3.7 |
| B | 196,300 | 6.0 |
| C | 276,500 | 8.0 |
| D | 401,300 | 12 |
| E | 2,000,000 | 32 |

EXAMPLE 15

Covalent coupling of horseradish peroxidase to DVS-activated hydroxy-ethyl-cellulose Purified horseradish peroxidase was covalently coupled to DVS-activated hydroxyethyl-cellulose with 818 µmoles of reactive vinyl sulfone groups per gram of hydroxyethyl-cellulose (prepared as described in Example 1). The coupling was performed at 4° C.

The procedure for coupling horseradish peroxidase was as follows:

100 mg of DVS-activated hydroxyethyl-cellulose (15.2 ml) was mixed with a solution of 400 mg of horseradish peroxidase (Kem-En-Tec, Copenhagen, Denmark) in 4.8 ml of water. To the mixture was then added 20 ml of 0.4M dipotassium hydrogen phosphate/sodium hydroxide (pH 10.6). The clear solution was incubated at 4° C. without stirring for 48 hours, after which the reaction was stopped by adjusting the pH of the solution to 6–7 with 1M hydrochloric acid.

The amount of coupled horseradish peroxidase was determined to be approx. 37% of the added horseradish peroxidase.

EXAMPLE 16

Covalent coupling of horseradish peroxidase to DVS-activated hydroxy-propyl-starch Purified horseradish peroxidase was covalently coupled to DVS-activated hydroxypropyl-starch with 2568 µmoles of reactive vinyl sulfone groups per gram of hydroxypropyl-starch (prepared as described in Example 2). The coupling was performed at 4° C.

The procedure for coupling horseradish peroxidase was as follows:

100 mg of DVS-activated hydroxypropyl-starch (15.6 ml of solution) was mixed with a solution of 400 mg of horseradish peroxidase in 4.4 ml of water. To the mixture was then added 20 ml of 0.4M dipotassium hydrogen phosphate/sodium hydroxide (pH 10.6).

The clear solution was incubated at 4° C. without stirring. Samples were withdrawn after 24 and 44 hours of incubation, and coupling yield was determined by gel filtration on Sephacryl™ S-200.

The amount of coupled horseradish peroxidase was determined to be approx. 20% of the added horseradish peroxidase after 24 hours of coupling and approx. 30% after 44 hours of coupling.

EXAMPLE 17

Covalent coupling of a peptide to DVS-activated bovine serum albumin

A synthetic peptide containing thirteen amino acid residues including a C-terminal cysteine was covalently coupled to DVS-activated bovine serum albumin.

The procedure for coupling the synthetic peptide was as follows:

0.5 ml of DVS-activated bovine serum albumin solution (prepared as described in Example 3) was mixed with 1 ml of peptide solution (7 mg/ml in 0.1M sodium chloride) and 0.5 ml of 3.0M dipotassium hydrogen phosphate (pH 8.5). The coupling mixture was incubated for 18 hours at room temperature without stirring.

Coupling yield was determined by gel filtration on 8% agarose gel (BioGel A-0.5m, BioRad), and the results were as follows: According to the gel filtration profile, 18% of the added peptide was coupled to the DVS-activated bovine serum albumin. This corresponds to approx. 12 moles of peptide per mole of DVS-activated BSA. This was in good agreement with the measured activity of DVS-activated BSA (see Example 3).

EXAMPLE 18

Covalent coupling of a peptide to DVS-activated dextran with peak MW 500,000

A synthetic peptide (the same as described in Example 17) containing thirteen amino acid residues including a C-terminal cysteine was covalently coupled to DVS-activated dextran of peak MW 500,000 with 490 µmoles of vinyl groups per gram of dextran ("batch Dex-I"; see Example 11).

The procedure for coupling the synthetic peptide was as follows: 0.5 ml of solution of the DVS-activated dextran (26 mg/ml) was mixed with 1 ml of peptide solution (3.5 mg/ml in 0.1M sodium chloride) and 0.5 ml of 3.0M dipotassium hydrogen phosphate (pH 8.5). The coupling mixture was incubated for 18 hours at room temperature without stirring.

Coupling yield was determined by gel filtration on 8% agarose gel (BioGel A-0.5m, BioRad), and the results were as follows:

According to the gel-filtration profile, approx. 98% of the added peptide was coupled to the DVS-activated dextran. This corresponds to approx. 88 moles of peptide per mole of DVS-activated dextran.

EXAMPLE 19

Covalent coupling of alkaline phosphatase (AP) to DVS-activated dextran with peak MW 500,000 at high temperature Purified alkaline phosphatase (Boehringer Mannheim, grade I, cat. No. 556602) was covalently coupled to DVS-activated dextran of peak MW 500,000. The DVS-activation was performed as described in Example 6, solution A (1% w/v dextran, 5% v/v divinyl sulfone), and the DVS-activated dextran contained 1500 µmoles of reactive vinyl groups per gram of dextran. The final concentration of DVS-activated dextran was 8 mg/ml. This batch of DVS-activated dextran is hereafter referred to as "batch Dex-II".

The procedure for coupling alkaline phosphatase was as follows: 0.03 ml of DVS-activated dextran ("batch Dex-II") was mixed with 0.2 ml of alkaline phosphatase solution (10 mg/ml), 0.16 ml of 2.0M dipotassium hydrogen phosphate (pH 9.5) and 0.01 ml of water. The clear solution was incubated at 37° C. without stirring.

Samples were withdrawn after different periods of incubation, and the percentage of the added alkaline phosphatase coupled to the dextran was determined by gel filtration on Sephacryl™ S-300 HR (Pharmacia, Sweden). The results were as follows:

From the relative area of the peaks, the following coupling efficiencies as a function of incubation time were determined [the results are given as percentage of the added alkaline phosphatase (AP) coupled, and calculated as moles of AP coupled per mole of dextran assuming a MW of 140,000 for AP and an average MW of 500,000 for the dextran]:

| Incubation time | coupling yield (%) | moles AP/mole dextran |
| --- | --- | --- |
| 2 hours | 24 | 7.2 |
| 4 hours | 31 | 9.2 |
| 6 hours | 39 | 12 |
| 24 hours | 51 | 15 |

EXAMPLE 20

Covalent coupling of alkaline phosphatase to DVS-activated dextran. The influence of salt concentration Alkaline phosphatase was coupled to DVS-activated dextran of peak MW 500,000 ("batch Dex-II"; see Example 19) at four different salt concentrations.

The procedure for coupling the alkaline phosphatase was as follows: Four different solutions (A–D) for coupling of alkaline phosphatase to DVS-activated dextran were prepared to give the following final concentrations:

All solutions contained:
5 mg of alkaline phosphatase/ml;
0.7 mg of DVS-activated dextran/ml;
dipotassium hydrogen phosphate/hydrochloric acid (pH 9.0).

The concentrations of dipotassium hydrogen phosphate were:
solution A: 0.10M
solution B: 0.25M
solution C: 0.50M
solution D: 0.80M The coupling was performed at 24° C. for 24 hours. The amount of coupled alkaline phosphatase was determined by gel filtration on Sephacryl™ S-300 HR. The results were as follows:

| Solution | coupling yield (%) | moles AP/mole dextran |
| --- | --- | --- |
| A | 3 | 0.8 |
| B | 5 | 1.3 |
| C | 11 | 2.8 |
| D | 24 | 6.1 |

EXAMPLE 21

Covalent coupling of alkaline phosphatase to DVS-activated dextran. The influence of pH Alkaline phosphatase was covalently coupled to DVS-activated dextran of peak MW 500,000 with 1500 µmoles of vinyl groups per gram of dextran ("batch Dex-II"). The coupling was performed at three different pH's.

The procedure for coupling alkaline phosphatase was as follows: Three dipotassium hydrogen phosphate buffers (A–C) for coupling alkaline phosphatase to DVS-activated dextran were prepared to give the following concentrations:

All solutions contained:
5 mg of alkaline phosphatase/ml;
0.6 mg of DVS-activated dextran/ml;
0.5M dipotassium hydrogen phosphate.

The pH of the phosphate buffers were:
solution A: pH 8.4
solution B: pH 9.5
solution C: pH 10.0

The clear solutions were incubated at 37° C. for 24 hours without stirring.

The percentage of the added alkaline phosphatase coupled to the dextran was determined by gel filtration on Sephacryl™ S-300 HR, and the results were as follows:

| Solution | coupling yield (%) | moles AP/mole dextran |
| --- | --- | --- |
| A | 10 | 3 |
| B | 45 | 13 |
| C | 79 | 24 |

EXAMPLE 22

Covalent coupling of alkaline phosphatase to DVS-activated dextran. The influence of temperature Purified alkaline phosphatase was coupled to DVS-activated dextran of peak MW 500,000 with 1500 µmoles of vinyl groups per gram of dextran ("batch Dex-II").

The procedure for coupling alkaline phosphatase was as follows: Alkaline phosphatase was coupled to DVS-activated dextran at three different temperatures (solutions A–C). The following concentrations and incubation times were used:

All solutions contained:
5 mg of alkaline phosphatase/ml;
0.6 mg of DVS-activated dextran/ml;
0.5M dipotassium hydrogen phosphate/sodium hydroxide (pH 10.0).

The following temperatures were employed:
solution A: 4° C.
solution B: 24° C.
solution C: 37° C.

Solution A was incubated for 24 hours, and solutions B and C were incubated for 4 hours.

The amount of coupled alkaline phosphatase was determined by gel filtration on Sephacryl™ S-300 HR, and the results were as follows:

| Solution | coupling yield (%) | moles AP/mole dextran |
|---|---|---|
| A | 20 | 6.0 |
| B | 23 | 6.8 |
| C | 47 | 14 |

EXAMPLE 23

Covalent coupling of alkaline phosphatase to DVS-activated dextrans with different degrees of activation Alkaline phosphatase was covalently coupled to three activated dextran preparations produced as described in Example 4 (solution B) and Example 6 (solution A and C) (the degrees of DVS-activation were 414 µmoles, 1500 µmoles and 2760 µmoles of vinyl sulfone groups per gram of dextran, respectively).

The procedure for coupling alkaline phosphatase was as follows: The three dextran preparations were mixed with alkaline phosphatase and buffer to give the following final concentrations:

5 mg of alkaline phosphatase/ml;
0.6 mg of DVS-activated dextran/ml and
A and B: 0.8M dipotassium hydrogen phosphate (pH 9.5);
C: 0.5M dipotassium hydrogen phosphate (pH 9.5).

The coupling was performed at 37° C. for 2 and 24 hours, respectively.

The amount of alkaline phosphatase coupled was determined by gel filtration on Sephacryl™ S-300 HR, and the results were as follows:

| Solution | µmoles vinyl groups/gram dextran | coupling yield (%) 2 hours | 24 hours |
|---|---|---|---|
| A | 414 | 15 | 33 |
| B | 1500 | 24 | 51 |
| C | 2760 | 12 | —* |

*when solution C was incubated for 24 hours, a gel precipitated in the reaction vessel.

EXAMPLE 24

Covalent coupling of an antibody to DVS-activated dextran at different pH's

Purified goat anti mouse Ig (DAKO A/S, Denmark, cat. No. Z420) was coupled to DVS-activated dextran of peak MW 500,000 containing 1500 µmoles vinyl sulfone groups per gram dextran ("batch Dex-II").

The procedure for coupling the Ig was as follows: Two dipotassium hydrogen phosphate buffers (A and B) for coupling goat anti mouse Ig to DVS-activated dextran were prepared to give the following concentrations:

All solutions contained:
6.9 mg of goat anti mouse Ig/ml;
0.9 mg of DVS-activated dextran/ml;
0.5M dipotassium hydrogen phosphate.

The pH of the buffers were:
solution A: pH 8.4
solution B: pH 9.5

The clear solutions were incubated at 24° C. for 24 hours.

The percentage of added goat anti mouse Ig coupled was determined by gel filtration on a Sephacryl™ S-300 HR, and the results were as follows:

| Solution | coupling yield (%) |
|---|---|
| A | 18 |
| B | —* |

*precipitation occurred in the reaction vessel.

EXAMPLE 25

Covalent coupling of an antibody to DVS-activated dextran at high and low temperature Goat anti mouse Ig (DAKO A/S, Denmark, cat. No. Z420) was covalently coupled to DVS-activated dextran of peak MW of 500,000 ("batch Dex-II") at two different temperatures.

The procedure for coupling the Ig was as follows: The goat anti mouse antibody was incubated at 4° C. and 24° C. under the following conditions:

All samples (A–C) contained:
6.9 mg of goat anti mouse Ig/ml;
0.9 mg of DVS-activated dextran/ml;
0.5M dipotassium hydrogen phosphate (pH 9.5).

Sample A and C were incubated for 24 hours, sample B for 48 hours.

The content of coupled antibody was determined by gel filtration on Sephacryl™ S-300 HR. From the relative area of the peaks, the following coupling efficiencies as a function of temperature were determined:

| Sample | temperature (°C.) | coupling yield (%) |
|---|---|---|
| A | 4 | 28 |
| B | 4 | 39 |
| C | 24 | —* |

*precipitation of a gel occurred in the sample at 24° C.

EXAMPLE 26

Covalent coupling of rabbit immunoglobulin to DVS-activated dextran (peak MW 500,000) at high temperature Normal rabbit immunoglobulin (DAKO A/S, Denmark, cat. No. X903) was coupled to DVS-activated dextran of peak MW 500,000 ("batch Dex-II") at high temperature.

The procedure for coupling the rabbit immunoglobulin was as follows: 1 ml of rabbit immunoglobulin preparation (20 mg/ml) was mixed with 0.32 ml of DVS-activated dextran and 0.44 ml of 2.0M dipotassium hydrogen phosphate (pH 9.5).

The clear solution was incubated at 24° C. without stirring.

Samples were withdrawn after different periods of incubation, and the percentage of added normal rabbit immunoglobulin coupled to the dextran was determined by gel filtration on Sephacryl™ S-300 HR. The results were as follows:

| Time of incubation | coupling yield (%) |
|---|---|
| 5 hours | 58 |
| 20 hours | —* |

*precipitation had occurred in the sample after 20 hours.

EXAMPLE 27

Covalent coupling of ammonia to DVS-activated dextran

Ammonia was covalently coupled to DVS-activated dextran of peak MW 500,000. The activation was performed as described in Example 4, solution E (5% w/v dextran, 0.5% v/v divinyl sulfone), and the DVS-activated dextran contained 86 µmoles of vinyl groups per gram of dextran. The final concentration of DVS-activated dextran was 22 mg/ml. This batch is hereafter referred to as "batch Dex-III".

The procedure for coupling ammonia was as follows: In a well ventilated hood, 50 ml of concentrated ammonia in water was added to 50 ml of DVS-activated dextran. The solution was heated to 60° C. and maintained at that temperature for 2 hours. The solution was then dialysed thoroughly against 4×5 liters of 0.5M sodium chloride over two days at room temperature.

After dialysis the volume had increased to 73 ml and the final concentration of dextran was therefore 15.1 mg/ml.

The content of amino groups coupled to the DVS-activated dextran was determined by acid-base titration to be approx. 80 µmoles per gram of dextran. The product is referred to in the following as "amino-dextran".

EXAMPLE 28

Covalent coupling of fluoresceinisothiocyanate (FITG) to amino-dextran

Fluoresceinisothiocyanate (Sigma, F-7250) was coupled to amino-dextran derived from dextran of peak MW 500,000. The amino-dextran (in solution) was prepared as described in Example 27.

The procedure for coupling fluoresceinisothiocyanate was as follows: 10 ml of amino-dextran solution were dialysed overnight against 2 liters of 0.1M sodium carbonate/bicarbonate (pH 9.5). After dialysis the volume was 9.5 ml and the final concentration of the dextran was 15.8 mg/ml.

30 mg of fluoresceinisothiocyanate was dissolved in dimethyl sulfoxide to a concentration of 10.0 mg/ml; 2.4 ml of this solution was added dropwise to 9.5 ml of the latter amino-dextran solution with stirring.

The reaction was allowed to proceed for 1.5 hours at room temperature, shielded from light.

After conjugation (coupling), unreacted or hydrolysed dye was removed by gel filtration on Sephadex™ G 25 (Pharmacia, Sweden).

The resulting solution was then dialysed against 0.1M dipotassium hydrogen phosphate (pH 7.2). After dialysis the volume was 23 ml and the final concentration of dextran was therefore 6.6 mg/ml.

The amount of fluoresceinisothiocyanate coupled to the amino-dextran was determined by absorbance measurements at 495 nm and 280 nm to be 68 moles of FITC per mole of dextran. The product is referred to in the following as "fluorescein-dextran".

EXAMPLE 29

DVS-activation of fluorescein-dextran

Fluorescein-dextran derived from dextran of peak MW 500,000 was reactivated (i.e. DVS-activated) with divinyl sulfone. The fluorescein-dextran (in solution) was prepared as described in Example 28.

The reactivation procedure was as follows: 10 ml of fluorescein-dextran solution was mixed with 10 ml of 0.5M dipotassium hydrogen phosphate/sodium hydroxide (pH 11.5) and 5 mg of sodium borohydride at room temperature.

Immediately after dissolution of the sodium borohydride, 1 ml of divinyl sulfone was added (in a well ventilated hood).

Gentle stirring was performed with a magnetic stirrer. After 60 minutes the pH of the mixture was adjusted to 6–7 with 5M hydrochloric acid to stop the reaction.

The solution was then dialysed against 4×2 liters of 0.5M sodium chloride, shielded from light.

After dialysis the volume had increased to 26 ml, and the final concentration of the DVS-activated fluorescein-dextran was therefore 2.5 mg/ml.

The content of reactive vinyl groups was determined by reaction with sodium thiosulfate followed by titration of the resulting hydroxide ions with standard hydrochloric acid (see Example 1).

The titration results indicated that the DVS-activated fluorescein-dextran contained 1080 µmoles of reactive vinyl groups per gram of dextran.

EXAMPLE 30

Covalent coupling of an antibody to DVS-activated fluorescein-dextran

Affinity-purified rabbit anti prostate-specific antigen antibodies (rabbit anti PSA) (DAKO A/S, Denmark, cat. No. A562) were coupled to reactivated fluorescein-dextran prepared as described in Example 29. The DVS-activated fluorescein-dextran contained 1080 µmoles of vinyl groups per gram of dextran and 35 moles of fluorescein per mole dextran.

The procedure for coupling rabbit anti prostate specific antigen antibodies was as follows: 1 ml of the solution of reactivated fluorescein-dextran was mixed with 18 ml of rabbit anti PSA preparation, after which 2.5M dipotassium hydrogen phosphate/sodium hydroxide (pH 10.0) was added to give a final concentration of 0.7M phosphate, pH 10.0.

The clear solution was incubated at 37° C. without stirring for 24 hours.

The content of coupled rabbit anti PSA was determined by gel filtration on Sephacryl™ S-300 to be approx. 20% of the added amount, corresponding to approx. 4 moles of antibody per mole of dextran.

EXAMPLE 31

Covalent coupling of avidin to DVS-activated dextran

Avidin from hens egg white (Kem-En-Tec, Denmark) was coupled to DVS-activated dextran with peak MW 500,000 ("batch Dex-I").

The procedure for coupling avidin was as follows: Avidin was mixed with the solution of DVS-activated dextran to give the following final concentrations:

3.0 mg of avidin/ml;
0.77 mg of DVS-activated dextran/ml;
0.8M dipotassium hydrogen phosphate/sodium hydroxide (pH 10.1).

The coupling mixture was incubated at 30° C. for 20 hours, followed by titration to pH 7 with 1M hydrochloric acid and dialysis for 24 hours against 5 liters of 0.1M sodium chloride.

Gel filtration on Sepharose™ Cl 6B (Pharmacia, Sweden) showed that 45% of the added avidin was coupled to the DVS-activated dextran. This corresponds to approx. 14 moles of avidin per mole of dextran with MW 500,000.

EXAMPLE 32

Covalent coupling of iminodiacetic acid to DVS-activated dextran

Iminodiacetic acid was coupled to DVS-activated dextran of peak MW 20,000, prepared according to Example 9.

The coupling procedure was as follows: Iminodiacetic acid was mixed with the solution of DVS-activated dextran to give the following final concentrations:

0.5M iminodiacetic acid,
30 mg of DVS-activated dextran/ml.

The mixture was titrated to pH 11.0 with 5M sodium hydroxide and incubated at room temperature for 24 hours. After incubation, the clear solution (127 ml) was dialysed thoroughly against water.

Acid-base titration of the dialysed solution indicated a content of approx. 1150 μmoles of iminodiacetic acid per gram of dextran. The product is referred to in the following as "iminodiacetic acid-dextran".

EXAMPLE 33

DVS activation of iminodiacetic acid-dextran

Iminodiacetic acid-dextran prepared according to Example 32 was reactivated with divinyl sulfone.

The reactivation procedure was as follows: 50 ml of iminodiacetic acid-dextran solution (16 mg/ml) was mixed with 50 ml of 0.5M dipotassium hydrogen phosphate (pH 11.5), 25 mg of sodium borohydride and 5 ml of divinyl sulfone.

The mixture was incubated at room temperature with stirring for 30 minutes and then titrated to pH 7 with 5M hydrochloric acid. The clear solution was then dialysed thoroughly against water.

After dialysis the concentration of DVS-activated iminodiacetic acid-dextran was 5 mg/ml, and reaction with thiosulphate followed by hydrochloric acid titration (see Example 1) revealed a content of 1320 μmoles of vinyl groups per gram of dextran.

EXAMPLE 34

Covalent coupling of bovine gammaglobulins to horseradish peroxidase-dextran as a function of salt concentration Bovine gammaglobulins (99% pure, Sigma, cat. No. G-5009) were coupled to remaining reactive vinyl sulfone groups of horseradish peroxidase-dextran prepared according to Example 12, using 192 hours of incubation.

The horseradish peroxidase-dextran used contained an average of 19 moles of horseradish peroxidase per mole of dextran of peak MW 500,000 and was purified to remove free horseradish peroxidase by gel filtration on 8% agarose gel (BioGel A-0.5m, BioRad). The concentration of horseradish peroxidase-dextran was calculated to be 5.8 mg/ml, corresponding to 3.5 mg of horseradish peroxidase/ml and 2.3 mg of dextran/ml. The product was dissolved in 0.1M sodium chloride containing 0.01% w/v of 1,1,1-trichloro-2-methyl-2-propanol (Sigma, cat. No. T 5138).

This batch of horseradish peroxidase-dextran is hereafter referred to as "batch HRP-Dex-I".

The coupling of bovine gammaglobulins was performed at different concentrations of dipotassium hydrogen phosphate to examine the effect of a lyotropic salt on the coupling efficiency.

The procedure for coupling bovine gammaglobulins was as follows:

Bovine gammaglobulin and horseradish peroxidase-dextran were mixed to give the following final concentrations:

7.88 mg of bovine gammaglobulin/ml;

2.57 mg of horseradish peroxidase-dextran/ml (corresponding to 1.02 mg of dextran/ml); and the following phosphate concentrations (as dipotassium hydrogen phosphate/sodium hydroxide, pH 10.1):

sample A: 010M
sample B: 020M
sample C: 035M
sample D: 050M
sample E: 070M
sample F: 090M The samples were incubated at room temperature for 20 hours. Following incubation, pH was adjusted to 7 with 1M hydrochloric acid.

The degree of coupling (coupling efficiency) in the various samples was then determined by gel filtration on Sepharose™ Cl 6B. Coupling efficiency was estimated from the change in the integrated UV-absorbance in the fractions containing the free and dextran-coupled protein, as well as by measuring the change in absorbance of the horseradish peroxidase-dextran at 280 nm and 403 nm before and after coupling. The following results were obtained:

| Sample | phosphate conc. | % gammaglobulin coupled | moles gammaglobulin/ mole dextran |
|---|---|---|---|
| A | 0.10 M | 18 | approx. 4.5 |
| B | 0.20 M | 20 | approx. 5.0 |
| C | 0.35 M | 19 | approx. 5.0 |
| D | 0.50 M | 24 | approx. 6.0 |
| E | 0.70 M | 30 | approx. 7.5 |
| F | 0.90 M | —* | — |

*at 0.9 M phosphate the protein conjugate precipitated irreversibly.

EXAMPLE 35

Covalent coupling of bovine gammaglobulin as a measure of retention of reactivity of horseradish peroxidase-dextran vinyl sulfone groups The long-term stability of the remaining vinyl sulfone groups on horseradish peroxidase-dextran prepared according to Example 12 was investigated by measuring the coupling capacity of horseradish peroxidase-dextran before and after incubation for 12 weeks at different temperatures.

The coupling efficiency for coupling of bovine gammaglobulins to horseradish peroxidase-dextran ("batch HRP-Dex I") was determined using coupling conditions as described for sample D in Example 34. The coupling efficiency was determined by gel filtration as described in Example 34 before and after incubation of the horseradish peroxidase-dextran at −20°, +4°, +20° and +30° C.

The coupling yield obtained before incubation is arbitrarily defined as 100%, and the results obtained after 12 weeks are expressed relative to this:

| Sample | incubation temperature °C. | relative coupling yield (%) |
|---|---|---|
| A | −20 | 110 |
| B | +4 | 95 |
| C | +20 | 80 |
| D | +30 | 70 |

EXAMPLE 36A

Coupling of rabbit anti mouse immunoglobulins to horseradish peroxidase-dextran. The influence of pH Rabbit anti mouse immunoglobulins (DAKO, Denmark, cat. No. Z259) were coupled to horseradish peroxidase-dextran at two different pH values. The horseradish peroxidase-dextran was prepared as described in Example 12 (48 hours at 4° C.) and contained 16 moles of peroxidase per mole of dextran.

The coupling procedure was as follows: Two different solutions for coupling of rabbit anti mouse immunoglobulins to horseradish peroxidase-dextran were prepared to give the following final concentrations:

All solutions contained:
1.9 mg of rabbit anti mouse Ig/ml;
HRP-dextran corresponding to 0.25 mg of dextran/ml;
0.5M dipotassium hydrogen phosphate titrated with either hydrochloric acid or sodium hydroxide to:
   solution A: pH 8.5
   solution B: pH 10.0

The clear solutions were incubated at 42° C. for 20 hours without stirring.

The percentage of the added rabbit anti mouse immunoglobulins coupled to the horseradish peroxidase-dextran was determined by gel filtration on Sephacryl™ S-300 HR, and the results were as follows:

| Solution | coupling yield (%) | moles RAM/mole dextran |
|---|---|---|
| A | 15 | 3.8 |
| B | 30 | 7.5 |

EXAMPLE 36B

Coupling of rabbit anti mouse immunoglobulins to horseradish peroxidase-dextran. The influence of temperature Rabbit anti mouse immunoglobulins (DAKO, Denmark, cat. No. Z259) were coupled to horseradish peroxidase-dextran. The HRP-dextran was prepared as described in Example 12 (48 hours at 4° C.) and contained 16 moles of horseradish peroxidase per mole of dextran.

The coupling procedure was as follows: Two solutions for coupling of rabbit anti mouse immunoglobulins to horseradish peroxidase-dextran were prepared to give the following final concentrations:

All solutions contained:
1.9 mg of rabbit anti mouse Ig/ml;
HRP-dextran corresponding to 0.25 mg of dextran/ml;
0.5M dipotassium hydrogen phosphate/sodium hydroxide (pH 10.0).

The clear solutions were incubated for 24 hours at:
Solution A: 22° C.
Solution B: 42° C.

The content of coupled rabbit anti mouse immunoglobulins was determined by gel filtration on Sephacryl™ S-300 HR, and the results were as follows:

| Solution | coupling yield (%) | moles RAM/mole dextran |
|---|---|---|
| A | 17.5 | 4.3 |
| B | 30.0 | 7.5 |

EXAMPLE 36C

Coupling of rabbit anti mouse immunoglobulins to horseradish peroxidase-dextran. The influence of the concentration of antibody and HRP-dextran Rabbit anti mouse immunoglobulins (DAKO, Denmark, cat. No. Z259) were coupled to horseradish peroxidase-dextran at five different concentrations of antibody and HRP-dextran, keeping the molar ratio of antibody to HRP-dextran constant (A–E). The HRP-dextran was prepared as described in Example 12 (48 hours at 4° C.) and contained 16 moles of horseradish peroxidase per mole of dextran.

The coupling procedure was as follows: Five different solutions (A–E) for coupling of rabbit anti mouse immunoglobulins to horseradish peroxidase-dextran were prepared to give the following final concentrations:

All solutions contained:
0.5M dipotassium hydrogen phosphate/sodium hydroxide (pH 10.0).

Solution A: 5.7 mg of rabbit anti mouse Ig/ml; HRP-dextran corresponding to 0.79 mg of dextran/ml.
Solution B: 6.7 mg of rabbit anti mouse Ig/ml; HRP-dextran corresponding to 0.92 mg of dextran/ml.
Solution C: 7.0 mg of rabbit anti mouse Ig/ml; HRP-dextran corresponding to 0.96 mg of dextran/ml.
Solution D: 7.2 mg of rabbit anti mouse Ig/ml; HRP-dextran corresponding to 1.00 mg of dextran/ml.
Solution E: 7.6 mg of rabbit anti mouse Ig/ml; HRP-dextran corresponding to 1.03 mg of dextran/ml.

The clear solutions were incubated at 24° C. for 20 hours.

The content of coupled rabbit anti mouse immunoglobulins was determined by gel filtration on Sephacryl™ S-300 HR.

From the relative areas of the peaks the following coupling efficiencies as a function of antibody concentration were determined:

| Solution | coupling yield (%) | moles RAM/mole dextran |
|---|---|---|
| A | 29 | 6.7 |
| B | 32 | 7.5 |
| C | 36 | 8.5 |
| D | 40 | 9.3 |
| E | partly precipitated precipitated | |

EXAMPLE 36D

Coupling of rabbit anti mouse immunoglobulins to different DVS-activated horseradish peroxidase-dextrans Rabbit anti mouse immunoglobulins (DAKO, Denmark, cat. No. Z259) were coupled to five different DVS-activated horseradish peroxidase-dextrans prepared as described in Example 13 (1500, 542, 234, 179 and 86 μmoles of vinyl groups per gram of dextran, respectively).

The coupling procedure was as follows: All five horseradish peroxidase-dextran preparations were mixed with rabbit anti mouse immunoglobulins and buffer to give the following final concentrations:

HRP-dextran corresponding to 0.2 mg of dextran/ml;

1.7 mg of rabbit anti mouse immunoglobulins/ml;
0.5M dipotassium hydrogen phosphate/sodium hydroxide (pH 10.0).

Coupling was performed at 42° C. for 20 hours without stirring.

The content of coupled rabbit anti mouse immunoglobulins was determined by gel filtration on Sephacryl™ S-300 HR, and the results were as follows:

| Solution | µmoles vinyl groups/ g dextran | moles HRP/ mole dextran | % RAM coupled | moles RAM/ mole dextran |
| --- | --- | --- | --- | --- |
| A | 1500 | 28 | 10 | 2.7 |
| B | 542 | 22 | 5 | 1.4 |
| C | 243 | 12 | ≈1 | 0.3 |
| D | 179 | 8.6 | ≈1 | 0.3 |
| E | 86 | 6.8 | ≈1 | 0.3 |

EXAMPLE 37A

Coupling of goat anti rabbit Ig to horseradish peroxidase-dextran

Affinity purified goat anti rabbit Ig was coupled to HRP-dextran ("batch HRP-Dex-I"; see Example 34).

Coupling conditions:

Antibody preparation and HRP-dextran solution were mixed to give the following final concentrations:

0.5M dipotassium hydrogen phosphate (pH 10.1)
2.0 mg goat anti rabbit Ig/ml
0.52 mg horseradish peroxidase-dextran/ml (corresponding to 0.21 mg dextran/ml)

The sample was incubated at 30° C. for 20 hours.

After coupling, glycine was added to the sample to a final concentration of 0.2M glycine, pH 10, and this was followed by incubation for 2 hours [resulting in deactivation (blocking) of remaining reactive vinyl sulfone groups by reaction thereof with glycine].

After incubation the sample was dialysed overnight at 4° C. against 0.05M Tris/HCl, 0.1M NaCl, pH 7.2.

The sample was then subjected to gel filtration on Sepharose™ CL 6B in order to separate free antibody and HRP-dextran-bound antibody.

Results:

The coupling yield for goat anti rabbit Ig was determined to be 25%, corresponding to 8 moles of goat anti rabbit Ig per mole of dextran (assuming the peak MW of the dextran to be 500,000 and the MW of the antibody to be 155,000). The final product thus contains an average of 8 moles of antibody and 19 moles of horseradish peroxidase per mole of dextran.

EXAMPLE 37B

Coupling of affinity-purified goat anti rabbit Ig together with "normal" goat immunoglobulin to horseradish peroxidase-dextran. Activity as a function of conjugate content of active antibody Affinity-purified goat anti rabbit Ig together with "normal" goat IgG (i.e. immunoglobulins from non-immunized goats) were coupled in various proportions to HRP-dextran. The purpose of the experiment was to examine the absorbance signal intensity obtainable (tested in ELISA) with the final dextran conjugates as a function of the average number of antigen-specific antibody molecules coupled to the dextran.

Coupling conditions:

Affinity-purified goat anti rabbit Ig, "normal" goat immunoglobulin and horseradish peroxidase-dextran ("batch HRP-Dex-I") were mixed to give the following final concentrations:

| Sample | affinity purified goat anti rabbit Ig (mg/ml) | "normal" goat IgG (mg/ml) |
| --- | --- | --- |
| A | 2.0 | 0 |
| B | 1.6 | 0.4 |
| C | 1.2 | 0.8 |
| D | 0.8 | 1.2 |
| E | 0.4 | 1.6 |
| F | 0 | 2.0 |

All samples:
0.5M dipotassium hydrogen phosphate (pH 10.1)
0.55 mg HRP-dextran/ml (corresponding to 0.22 mg dextran/ml).

The samples were incubated at 30° C. for 20 hours.

After coupling, glycine was added to the samples to a final concentration of 0.2M glycine, pH 10, and this was followed by incubation for 2 hours [resulting in deactivation (blocking) of remaining reactive vinyl sulfone groups by reaction thereof with glycine].

After incubation the samples were dialysed overnight at 4° C. against 0.05M Tris/HCl, 0.1M NaCl, pH 7.2.

The samples were then subjected to gel filtration on Sepharose™ CL 6B in order to separate the free immunoglobulins and HRP-dextran-bound immunoglobulins.

Results:

The coupling yield—assuming the same coupling reactivity of the two goat immunoglobulin preparations—was determined to be approx. 22%, corresponding to an average total of 6.5 moles of goat immunoglobulin per mole of dextran. Again assuming the same coupling reactivity for the two types of immunoglobulins, the final average number of moles of each type of immunoglobulin per mole of dextran was as follows:

| Sample | moles affinity-purified goat anti rabbit Ig/mole dextran | moles "normal" goat IgG/mole dextran |
| --- | --- | --- |
| A | 6.5 | 0 |
| B | 5.2 | 1.3 |
| C | 3.9 | 2.6 |
| D | 2.6 | 3.9 |
| E | 1.3 | 5.2 |
| F | 0 | 6.5 |

ELISA results:

The six dextran conjugates were characterized in ELISA (according to "General ELISA procedure", three layers).

ELISA conditions:

1st layer:
Goat anti rabbit Ig (1 µg/ml) diluted in dipotassium hydrogen phosphate (pH 7.2).

2nd layer:
Rabbit IgG (1 ng/ml) Diluted in 0.1M dipotassium hydrogen phosphate, 0.5M NaCl, 1% Tween™ 20 (pH 7.2).

3rd layer:
Serial dilutions of the six conjugates in 0.1M dipotassium hydrogen phosphate, 1% Tween™ 20 (pH 7.2).

Figure 2:
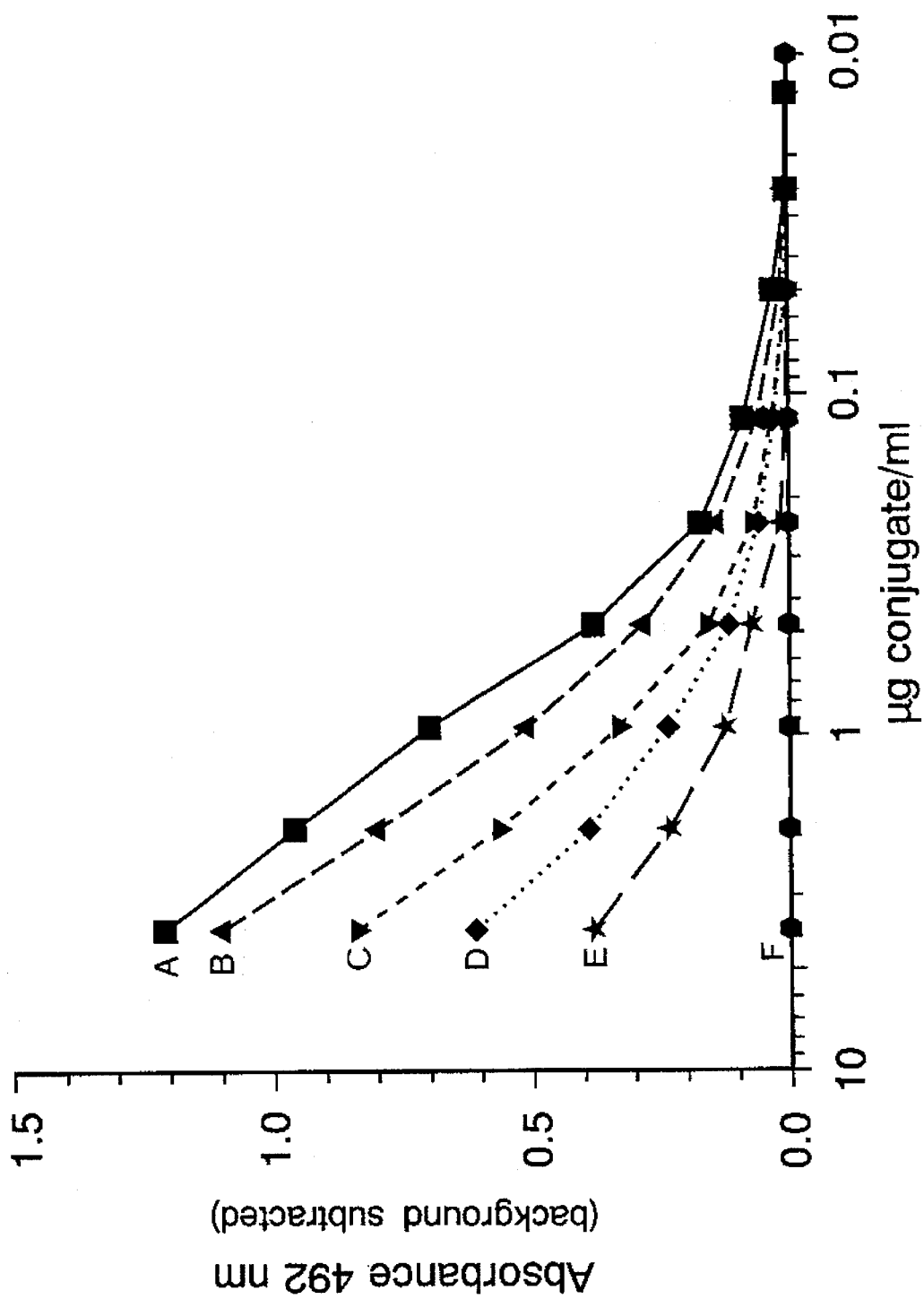
FIG. 2: Results from Example 37B. Relationship between the concentration of HRP-dextran/goat anti rabbit IgG conjugates and the absorbance at 492 nm in a three-layer ELISA. Results are shown for conjugates comprising various combinations of numbers of goat anti rabbit IgG molecules and of molecules of immunoglobulin from non-immunized goats per molecule of dextran. It is apparent that for a given concentration of conjugate, the measured absorbance increases with increase in the number of conjugated goat anti rabbit IgG molecules per molecule of dextran.

As can be seen from FIG. 2, there is a clear relationship between the number of goat anti rabbit antibodies coupled and the intensity of the absorbance signal obtained in ELISA. The absence of goat anti rabbit antibodies on the dextran results in lack of signal, as expected.

EXAMPLE 37C

Characterisation of HRP-dextran/goat anti rabbit Ig in ELISA and in Dot Blots

Goat anti rabbit Ig coupled to HRP-dextran and subjected to gel filtration on Sepharose™ CL 6B as described in Example 37A was characterized in ELISA and in Dot Blots. For comparison, a "conventional" conjugate (HRP-labelled swine anti rabbit Ig; DAKO A/S, Denmark, cat. No. P217) was subjected to the same procedures.

ELISA (according to "General ELISA procedure")

1st layer:
Goat anti rabbit Ig (1 µg/ml) in 0.1M dipotassium hydrogen phosphate (pH 7.2);

2nd layer:
Rabbit IgG (1 ng/ml) diluted in 0.1M dipotassium hydrogen phosphate, 1% Tween™ 20 (pH 7.2);

3rd layer:
Serial dilution of HRP-dextran/goat anti rabbit Ig or HRP-labelled swine anti rabbit Ig (DAKO A/S, Denmark, cat. No. P217) in 0.1M dipotassium hydrogen phosphate, 1% Tween™ 20 (pH 7.2).

Figure 3:
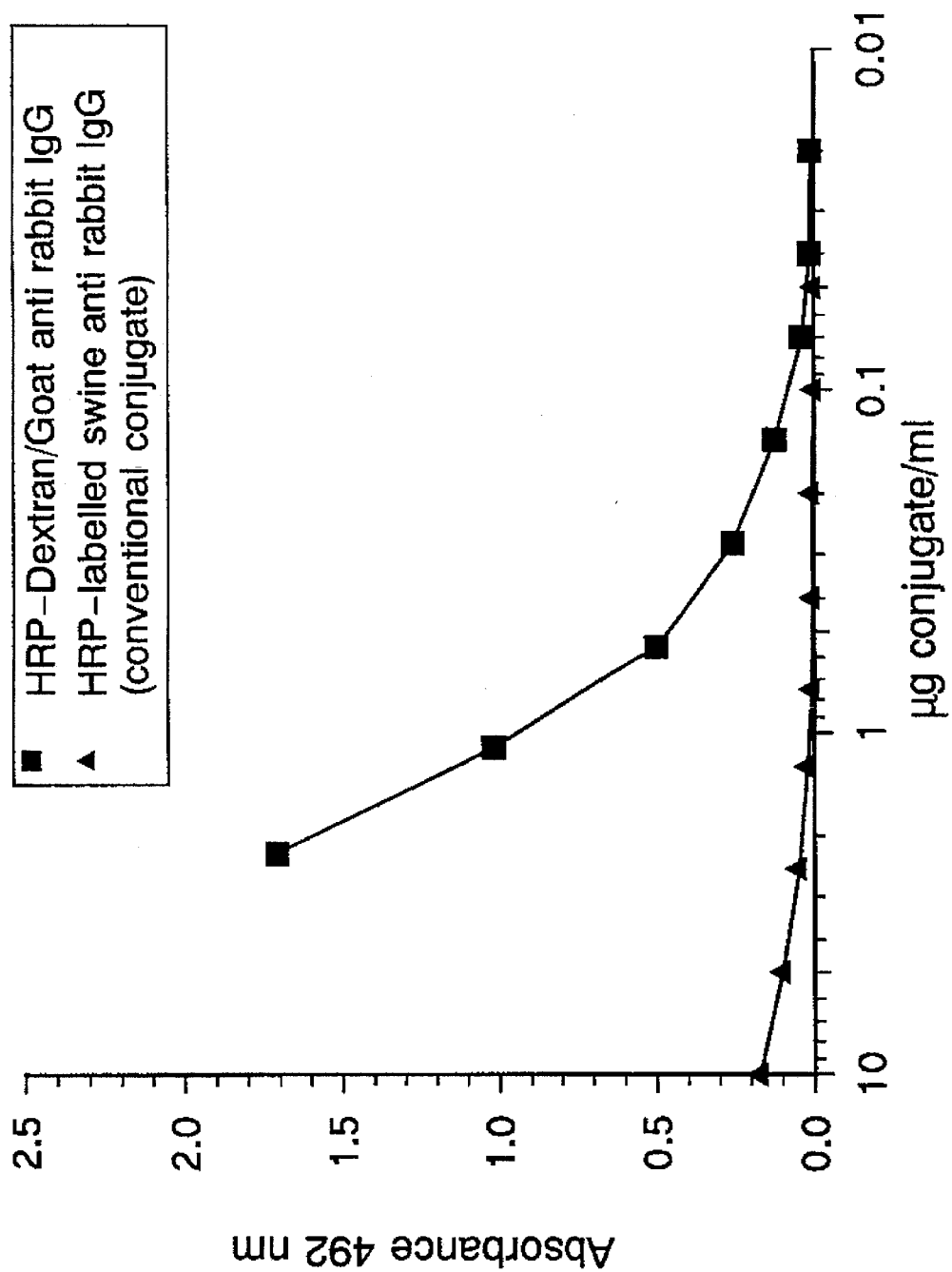
FIG. 3: Results from Example 37C. Relationship between the concentration of a HRP-dextran/goat anti rabbit IgG conjugate and the absorbance at 492 nm in a three-layer ELISA. For comparison purposes, results are also shown for a conventional HRP-labelled (conjugated) swine anti rabbit IgG. It is apparent that for a given concentration, the measured absorbance is considerably higher for the dextran conjugate according to the invention than for the conventional conjugate.

Results:
As can be seen from FIG. 3, the dextran-based conjugate can be diluted much more than the conventional conjugate and still give rise to a significant signal, indicating the increased sensitivity obtainable using the conjugate of the invention as reagent.

Dot Blots (according to "General procedure for Dot Blot"):

Results:
The HRP-dextran/goat anti rabbit Ig conjugate according to the invention gave a 10-fold increase in sensitivity relative to the conventional conjugate (i.e. it could detect a 10 times smaller amount of rabbit IgG in dots).

EXAMPLE 38

Coupling of avidin to horseradish peroxidase-dextran

Avidin from hens egg white was coupled to HRP-dextran ("batch HRP-Dex-I"; see Example 34) at different concentrations and molar ratios of avidin to HRP-dextran.

Coupling conditions:
The following components were mixed:
(a) avidin 25 mg/ml
(b) HRP-dextran corresponding to 0.52 mg of dextran/ml
(c) 2M $K_2HPO_4$/NaOH pH 10.0
(d) Water All couplings were carried out at a phosphate concentration of 0.82M. The concentrations of avidin and HRP-dextran are shown in the following:

| Sample No. | Avidin mg/ml | HRP-dextran mg/ml | Molar ratio (avidin:HRP-dextran) in solution |
|---|---|---|---|
| 1 | 0.3 | 0.27 | 2 |
| 2 | 1.1 | 0.27 | 8 |
| 3 | 4.2 | 0.27 | 30 |
| 4 | 17.0 | 0.27 | 120 |

The molar ratio is given as moles of avidin per mole of HRP-dextran in the coupling solution.

The coupling samples were incubated at 30° C. for 20 hours.

After coupling, the samples were dialysed against water for 2 hours at room temperature.

The samples were then subjected to gel filtration on Sepharose™ CL-6B in order to separate free and HRP-dextran-bound avidin.

Results of the couplings:
The content of coupled avidin in the resulting conjugates was found to increase with increasing molar ratio of avidin to HRP-dextran and approach a plateau value, there being very little increase above a molar ratio of 30. The results are shown in the following:

| Sample No. | Molar ratio (avidin:HRP-dextran) | Moles avidin coupled/ mole dextran |
|---|---|---|
| 1 | 2 | 2 |
| 2 | 8 | 6 |
| 3 | 30 | 11 |
| 4 | 120 | 12 |

Test in ELISA
The detection sensitivity obtainable with the peroxidase-dextran/avidin conjugates as a function of the number of avidin molecules incorporated in the conjugates was tested in ELISA.

With reference to the "General ELISA procedure", the following set-up was used:
layer 1: Goat anti rabbit IgG; 0.025 mg/ml;
layer 2: Serial dilution of biotinylated rabbit IgG;
layer 3: HRP-dextran/avidin conjugates; each conjugate diluted to the same protein concentration, i.e. to a absorbance value at 280 nm ($A_{280}$) of 0.00063.

Figure 4:
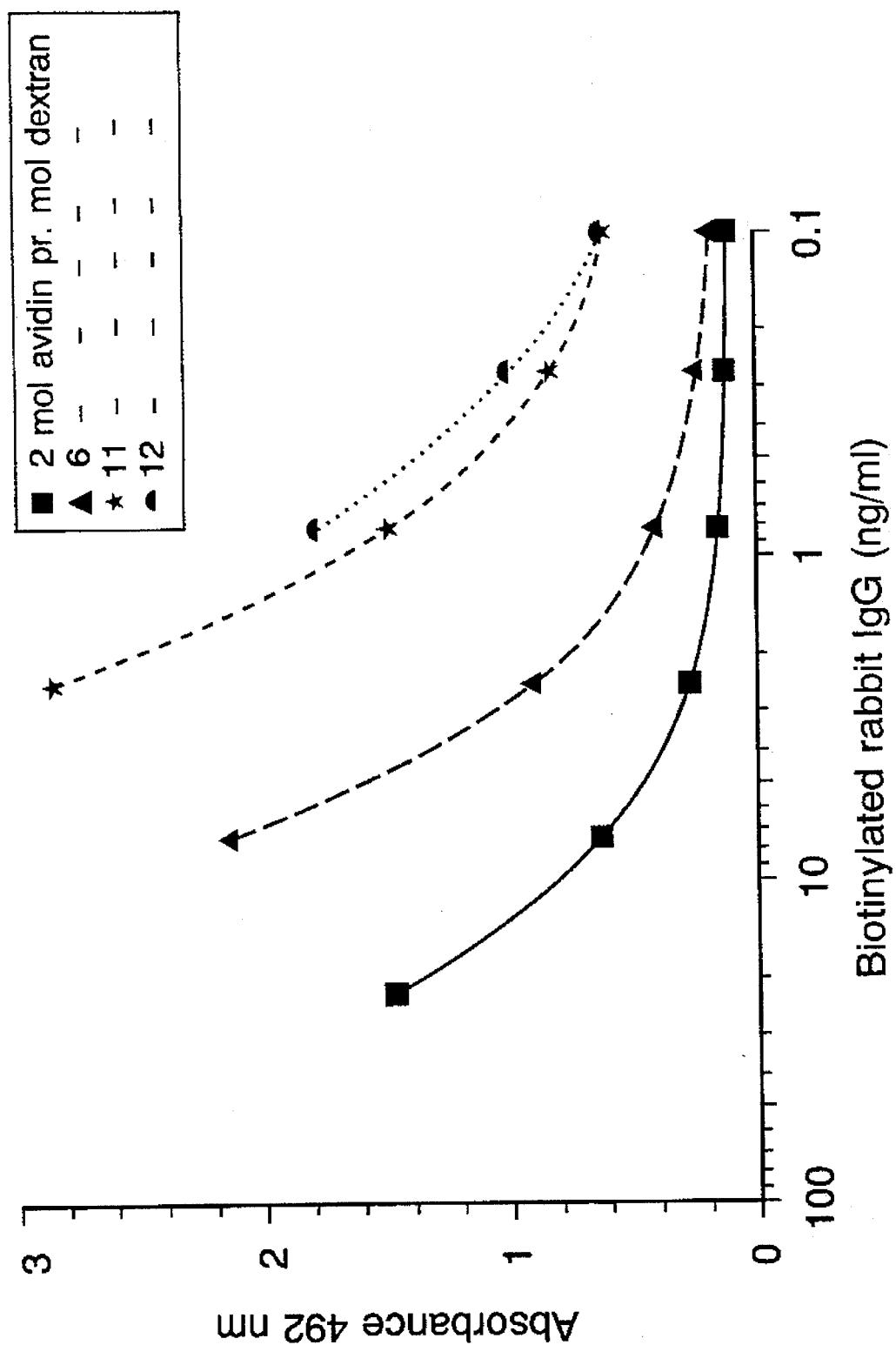
FIG. 4: Results from Example 38. Relationship between the concentration of biotinylated rabbit IgG in the second layer in a three-layer ELISA, and the absorbance at 492 nm using HRP-dextran/avidin conjugates to detect the biotinylated rabbit IgG. Results are shown for four HRP-dextran/avidin conjugates comprising different numbers of avidin molecules per molecule of dextran. It is apparent that for a given concentration of biotinylated rabbit IgG, the measured absorbance increases with increase in the number of conjugated avidin molecules per molecule of dextran.

ELISA results:
FIG. 4 shows the absorbance at 492 nm as a function of the concentration of biotinylated rabbit IgG in layer 2:

The curves in FIG. 4 show that the detection sensitivity obtainable with the conjugates increases with the number of coupled avidin molecules. That is, when the number of coupled avidin molecules is increased, smaller amounts of biotinylated rabbit IgG can be detected.

EXAMPLE 39

Coupling of streptavidin to horseradish peroxidase-dextran

Affinity-purified streptavidin was coupled to HRP-dextran ("batch HRP-Dex-I"; see Example 34) in media containing different concentrations of dipotassium hydrogen phosphate (pH 10.1).

Coupling conditions:
The following media were employed:

| | |
|---|---|
| 1: | 0.01 M dipotassium hydrogen phosphate (pH 10.1) |
| 2: | 0.80 M dipotassium hydrogen phosphate (pH 10.1) |
| 3: | 1.00 M dipotassium hydrogen phosphate (pH 10.1) |

All samples:
4.0 mg streptavidin/ml
4.1 mg HRP-dextran/ml (corresponding to 2.3 mg dextran/ml)

The samples were incubated at 30° C. for 20 hours.

After coupling, glycine was added to the samples to a final concentration of 0.2M glycine, pH 10, and this was followed by incubation for 2 hours [resulting in deactivation (blocking) of remaining reactive vinyl sulfone groups by reaction thereof with glycine].

After incubation the samples were dialysed overnight at 4° C. against 0.05M Tris/HCl, 0.1M NaCl, pH 7.2.

The samples were then subjected to gel filtration on Sepharose™ CL 6B in order to separate the free streptavidin and HRP-dextran-bound streptavidin.

Results:

The coupling yield for streptavidin (assuming the average molecular weight of the dextran to be 500,000 and the molecular weight of streptavidin to be 60,000) was determined to be:

1: 16%, corresponding to 5 moles of streptavidin/mole of dextran

2: 46%, corresponding to 14 moles of streptavidin/mole of dextran

3: — (precipitation occurred in the reaction vessel after 1 h).

The final products thus contain an average of:

1: 5 moles of streptavidin and 19 moles of peroxidase per mole of dextran.
2: 14 moles of streptavidin and 19 moles of peroxidase per mole of dextran.
3: —

EXAMPLE 40

Characterisation of HRP-dextran/streptavidin in ELISA and Dog Blot

Streptavidin was coupled to HRP-dextran according to Example 39, sample 2 (0.8M $K_2HPO_4$).

After gel filtration on Sepharose™ CL 6B the HRP-dextran-bound streptavidin was characterised in ELISA and Dot Blot.

For comparison, a conventional conjugate of streptavidin and horseradish peroxidase (cat. No.: P317, DAKO, Denmark) was tested in parallel.

ELISA (according to "General ELISA procedure", 2 layers)

ELISA conditions:

layer 1:

Serial dilution of biotin-conjugated rabbit IgG in 0.1M dipotassium hydrogen phosphate (pH 7.2).

layer 2:

One dilution of HRP-dextran/streptavidin (0.014 mg/ml) or conventional streptavidin-peroxidase (0.02 mg/ml) (DAKO A/S, Denmark, cat. No. P397) in 0.1M dipotassium hydrogen phosphate, 1% Tween™ 20 (pH 7.2).

Figure 5:
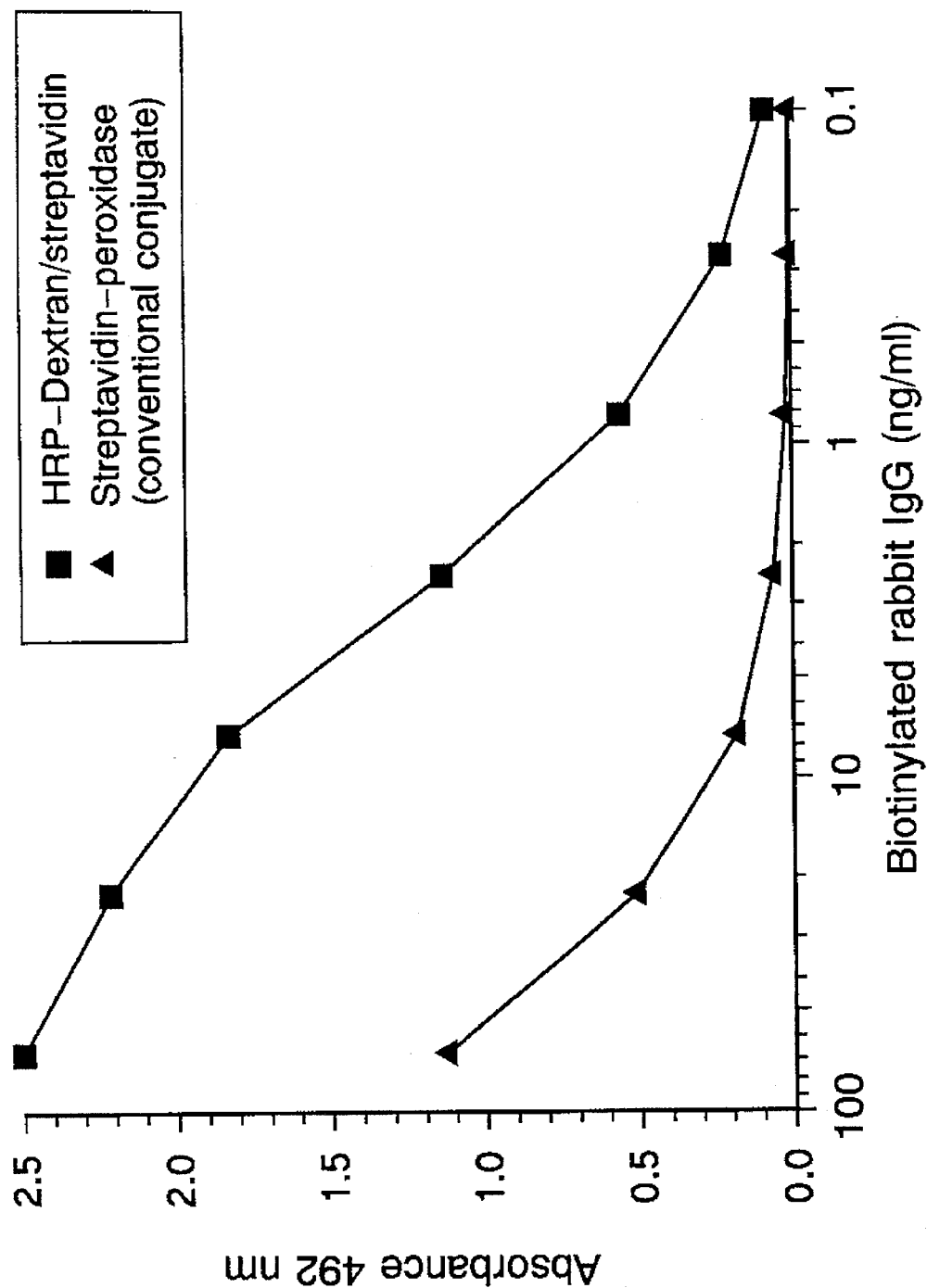
FIG. 5: Results from Example 40. Relationship between the concentration of biotinylated rabbit IgG used for the first layer (i.e. for adsorption to the surface of the solid-phase support) in a two-layer ELISA, and the absorbance at 492 nm. Results are shown for a HRP-dextran/streptavidin conjugate according to the invention and, for comparison purposes, for a conventional HRP-labelled (conjugated) streptavidin. It is apparent that for a given concentration of biotinylated rabbit IgG, the measured absorbance is considerably higher for the dextran conjugate according to the invention than for the conventional conjugate, i.e. the detection limit in the assay is significantly lower when the conjugate of the invention is used than when the conventional conjugate is used.

Results:

As can be seen from FIG. 5, the dextran-based conjugate according to the invention gives a significantly lower detection limit than the conventional conjugate.

Dot Blots:

Dot Blot conditions (according to "General procedure for Dot Blot"):

Results:

Using the HRP-dextran/goat anti rabbit Ig conjugate according to the invention it was possible to detect a 10 times smaller amount of biotinylated rabbit IgG in the dots than with the conventional conjugate.

EXAMPLE 41

Covalent coupling of an antibody to alkaline phosphatase-dextran

Purified rabbit anti mouse Ig (RAM) (DAKO A/S, Denmark, cat. No. Z259) was coupled to three different AP-dextran preparations (alkaline phosphatase was coupled to the dextrans as described in Example 22, solutions A and B, and Example 23, solution B).

The procedure for coupling the antibody was as follows:

the three different AP-dextrans (A–C) prepared for coupling of RAM were as follows:

A: 6 moles of alkaline phosphatase/mole of dextran;
B: 7 moles of alkaline phosphatase/mole of dextran;
C: 15 moles of alkaline phosphatase/mole of dextran.

The three coupling samples (samples A–C) prepared using these three AP-dextrans (A–C, respectively) all contained:

1.55 mg of RAM/ml;

AP-dextran corresponding to 0.2 mg of dextran/ml;

0.5M dipotassium hydrogen phosphate/sodium hydroxide (pH 10.0).

The samples were incubated at 37° C. for 24 hours.

The content of coupled RAM in the resulting conjugates was determined by gel filtration on Sephacryl™ S-300 HR, and the results were as follows:

| Sample | coupling yield (%) | mole RAM/mole dextran |
|---|---|---|
| A | 44 | 11 |
| B | 42 | 10.5 |
| C | 24 | 6 |

EXAMPLE 42

Covalent coupling of alkaline phosphatase to antibody-dextran

Three different antibody-dextran preparations were coupled with alkaline phosphatase. The antibody, viz. goat anti mouse Ig (DAKO A/S, Denmark, cat. No. Z420), was coupled to DVS-activated dextran as described in Example 24, solution A, and in Example 25, solutions A and B.

The procedure for coupling alkaline phosphatase was as follows: Each of the three different preparations of antibody-dextrans was mixed with alkaline phosphatase and buffer to give the following final concentrations:

All samples contained:

2.0 mg of alkaline phosphatase/ml;

antibody-dextran corresponding to 0.29 mg of dextran/ml;

0.8M dipotassium hydrogen phosphate/hydrochloric acid (pH 9.0).

Sample A: 4.5 moles of goat anti mouse Ig/mole of dextran

Sample B: 7 moles of goat anti mouse Ig/mole of dextran

Sample C: 10 moles of goat anti mouse Ig/mole of dextran

The coupling was performed at 24° C. for 22 hours with gentle shaking.

The degree of AP coupling was determined by gel filtration on Sephacryl™ S-300 HR, and the results were as follows:

| Sample | coupling yield (%) | moles AP/mole dextran |
|---|---|---|
| A | <10 | <2.5 |
| B | <10 | <2.5 |
| C | —* | — |

*precipitation of a gel occurred in sample C.

EXAMPLE 43

Coupling of Fab' fragments to alkaline phosphatase-dextran. The influence of salt concentration and temperature Fab' fragments [a Fab' fragment is an antibody fragment comprising one antigen-binding site and one free SH group; such fragments are produced by treating an antibody molecule with pepsin (to form a so-called $F(ab')_2$ fragment) and then with DTT] prepared from goat anti mouse Ig (DAKO A/S, Denmark, cat. No. Z420) according to A. Johnstone and R. Thorpe, "Immunochemistry in Practice", 2nd edition, 1987, pp. 57–58, were coupled to AP-dextran as described in Example 20, solution D (24 hours).

The coupling procedure was as follows: A solution for coupling of goat anti mouse Fab'-fragments to AP-dextran was prepared to give the following final concentrations:

0.63 mg of goat anti mouse Fab'-fragments/ml;
AP-dextran corresponding to 0.196 mg of dextran/ml;
Samples A and B: 0.5M dipotassium hydrogen phosphate/hydrochloric acid (pH 8.0);
Samples C and D: 0.75M dipotassium hydrogen phosphate/hydrochloric acid (pH 8.0).

The clear solutions were incubated with gentle shaking for 24 hours at:
A and C: 24° C.,
B and D: 30° C.

After incubation, the content of coupled goat anti mouse Fab' fragments was determined by gel filtration on Sephacryl™, and the results were as follows:

| Sample | coupling yield (%) | moles Fab'/mole dextran |
|---|---|---|
| A (0.5 M phosphate, 24° C.) | 38 | 13.3 |
| B (0.5 M phosphate, 30° C.) | 42 | 14.7 |
| C (0.75M phosphate, 24° C.) | 50 | 17.3 |
| D (0.75M phosphate, 30° C.) | 49 | 17.2 |

EXAMPLE 44

Coupling of Fab' fragments Co horseradish peroxidase-dextran. The influence of pH Fab' fragments prepared from goat anti rabbit F(ab')$_2$ fragments (according to A. Johnstone and R. Thorpe, "Immunochemistry in Practice", 2nd edition, 1987, pp. 57–58) were coupled to HRP-dextran, produced as described in Example 12 (48 hours), at five different pH's.

The coupling procedure was as follows: Five different solutions (A–E) for coupling Fab' fragments to HRP-dextran were prepared to give the following final concentrations:

All samples contained:
0.67 mg of goat anti rabbit Fab' fragments/ml;
HRP-dextran corresponding to 0.29 mg of dextran/ml;
0.50M dipotassium hydrogen phosphate/hydrochloric acid.

The pH values of the dipotassium hydrogen phosphate buffers were:
sample A: pH 5.0
sample B: pH 6.0
sample C: pH 7.0
sample D: pH 8.0
sample E: pH 9.0

The five clear solutions were incubated at 24° C. for 20 hours with gentle shaking.

The degree of coupling of Fab' fragments was determined by gel filtration on Sephacryl™ S-300 HR, and the results were as follows:

| Sample | coupling yield (%) | moles Fab'/mole dextran |
|---|---|---|
| A | 10 | 2.6 |
| B | 22 | 5.5 |
| C | 52 | 13 |
| D | 64 | 16 |
| E | 100 | 25 |

EXAMPLE 45

Thiolation of alkaline phosphatase

Alkaline phosphatase (AP) with MW 140,000 (Boehringer Mannheim, cat. No. 556602, grade 1) was thiolated with N-succinimidyl 3-(2-pyridyldithio)propionate (SPDP) (Pharmacia, Sweden, cat. No. 17-0458-01).

For the present purposes the general procedure for thiolation of proteins first described by Carlsson et al., Biochem. J. (1978) 173 723–737, was further developed as follows:

Thiolation procedure:

To 1.0 ml of alkaline phosphatase preparation [10 mg/ml in 3M NaCl, 1 mM MgCl$_2$, 0.1 mM ZnCl$_2$, 30 mM triethanolamine (pH 7.6)] was added and 28.6 µl of SPDP (10 mM in 99.9% ethanol) (the amount of SPDP added can be varied and depends on the desired degree of substitution, i.e. number of moles of 2-pyridyl disulphide structures per mole of AP). The SPDP solution was added dropwise to the stirred AP solution, and the reaction mixture was then incubated for about 30 minutes at 24° C.

After the incubation a small sample (50–100 µl) was withdrawn and subjected to gel filtration on Sephadex™ G-25 with 0.05M Tris/HCl buffer containing 0.1M NaCl, 1 mM MgCl$_2$ and 0.1 mM ZnCl$_2$ (pH 7.2), to remove excess SPDP, liberated N-hydroxysuccinimide and any other material of low molecular weight.

The gel filtered sample was used to determine the content of 2-pyridyl disulphide structures (=the final content of thiol groups) in the modified AP, and was treated as follows:

The absorbance at 280 nm and 343 nm was measured, after which dithiothreitol (DTT) was added to a final concentration of 10 mM. After incubation for 10 minutes at 23° C. the absorbance at 343 nm was measured again.

The treatment with DTT effects the release of pyridine-2-thione, which has an absorptivity of $8.08 \times 10^3 M^{-1} cm^{-1}$ at 343 nm.

The amount of pyridine-2-thione released is equivalent to the content of 2-pyridyl disulphide groups in the AP. Since the 2-pyridyl disulphide group itself exhibits absorption at 280 nm, an erroneously high protein concentration will be obtained if calculated on the basis of the measured absorbance at 280 nm ($A_{280}$). This additional absorbance can be corrected for by subtracting the $A_{280}$ contribution of the 2-pyridyl disulphide group from the total $A_{280}$. The former contribution is calculated using the following expression: (concentration of pyridine-2-thione released on reduction)× $5.1 \times 10^3 M^{-1} cm^{-1} = A_{280}$ due to the 2-pyridyl disulphide group ($5.1 \times 10^3 M^{-1} cm^{-1}$ is the molar absorptivity at 280 nm for the 2-pyridyl disulphide group).

The content of 2-pyridyl disulphide structures (=the final content of thiol groups) in the modified AP was determined as described above for 10 different thiolations of AP. Each sample was treated as described above (i.e. 4 moles of SPDP/mole of AP during the incubation) and a content of 1.85±0.25 moles of 2-pyridyl disulphide/mole of AP was obtained.

Meanwhile, the rest of the mixture of the 2-pyridyl disulphide modified AP (not subjected to gel filtration) was treated with DTT in order to reduce the protein-coupled 2-pyridyl disulphide structures. This was done in the same way as described above, i.e. DTT was added to a final concentration of 10 mM and the mixture was incubated at 20°–23° C. for about 5–10 minutes. Reduction of the introduced 2-pyridyl disulphide structures takes place very rapidly (<1–2 minutes) with DTT at pH 7.2, and as the native —S—S— bridges of AP are buried deeply within the internal structure of AP they will not be reduced by this treatment.

After reduction, the thiolated AP was separated from material of low molecular weight by gel filtration on Sephadex™ G-25 (using PD-10 columns) with the desired coupling buffer and was used shortly thereafter (within an hour) for coupling, since the thiol group is very reactive and can undergo unwanted reactions. The modified AP must therefore be stored in the 2-pyridyl disulphide form (if necessary overnight at 4° C. in the above mentioned Tris/HCl buffer) and reduced just before use.

A content of 1.85±10.25 moles of 2-pyridyl disulphide structures/mole of AP results in no loss of AP activity, and the subsequent reduction with DTT results in a loss of only about 51 of the original AP activity.

EXAMPLE 46

Coupling of Thiolated AP to DVS-activated dextran. The influence of pH

Thiolated AP (SH-AP) was coupled to DVS-activated dextran of peak MW 500,000 with 1500 μmoles of vinyl groups per gram of dextran ("batch Dex-II"). The thiolated AP was produced as described in Example 45 and contained a mean of 2.1 moles of SH groups/mole of alkaline phosphatase.

The coupling procedure was as follows: Three different solutions (A–C) for coupling of thiolated AP to DVS-activated dextran were prepared to give the following final concentrations:

All solutions contained:
2.0 mg of thiolated AP/ml;
0.286 mg of DVS-activated dextran/ml;
0.50M dipotassium hydrogen phosphate/hydrochloric acid;

The pH values of the dipotassium hydrogen phosphate buffers were:
solution A: pH 7.0
solution B: pH 8.0
solution C: pH 8.5.

The clear solutions were incubated at 24° C. for 24 hours with gentle shaking.

The content of coupled thiolated AP was determined by gel filtration on Sephacryl™ S-300 HR, and the results were as follows:

| Solution | coupling yield (%) | moles SH-AP/ mole dextran |
|---|---|---|
| A | 39 | 9.8 |
| B | 77 | 19.2 |
| C | 82 | 20.5 |

EXAMPLE 47

Coupling of thiolated AP to DVS-activated dextran. The influence of time and temperature Thiolated AP (SH-AP) was coupled to DVS-activated dextran of peak MW 500,000 with 1500 μmoles of vinyl groups per gram of dextran ("batch Dex-II"). The thiolated AP was produced as described in Example 45 and contained a mean of 2 moles of SH groups/mole of alkaline phosphatase.

The coupling procedure was as follows: A solution for coupling of thiolated AP to DVS-activated dextran was prepared to give the following final concentrations:
1.0 mg of thiolated AP/ml;
0.143 mg of DVS-activated dextran/ml;
0.5M dipotassium hydrogen phosphate/hydrochloric acid (pH 8.0).

The clear solution was incubated for 4 hours at 24° C. with gentle shaking and then for 144 hours at 4° C. without shaking.

Samples were withdrawn after different periods of incubation and the content of coupled SH-alkaline phosphatase was determined by gel filtration on Sephacryl™ S-300 HR. The results were as follows:

| Hours | coupling yield (%) | moles SH-AP/mole dextran |
|---|---|---|
| 0 | 0 | 0 |
| 1 | 8 | 1.9 |
| 2 | 12 | 3.1 |
| 4 | 25 | 6.3 |
| +144 (4° C.) | 58 | 14.4 |

EXAMPLE 48

Coupling of thiolated AP to DVS-activated dextran. The influence of salt concentrations Thiolated AP (SH-AP) was coupled to DVS-activated dextran of peak MW 500,000 with 1500 μmoles of vinyl groups per gram of dextran ("batch Dex-II"). The thiolated AP was produced as described in Example 45 and contained a mean of 1.6 moles of SH groups/mole of alkaline phosphatase.

The coupling procedure was as follows: Four different solutions (A–D) for coupling of thiolated AP to DVS-activated dextran were prepared to give the following final concentrations:

All solutions contained:
2.20 mg of thiolated AP/ml;
0.314 mg of DVS-activated dextran/ml;
dipotassium hydrogen phosphate/hydrochloric acid (pH 8.0).

The concentrations of dipotassium hydrogen phosphate in the buffers were:
solution A: 0.10M
solution B: 0.25M
solution C: 0.50M
solution D: 0.75M The clear solutions were incubated at 24° C. for 24 hours with gentle shaking.

The content of coupled thiolated AP was determined by gel filtration on Sephacryl™ S-300 HR, and the results were as follows:

| Solution | coupling yield (%) | moles SH-AP/mole dextran |
|---|---|---|
| A | 57 | 14.3 |
| B | 67 | 16.7 |
| C | 77 | 19.3 |
| D | 78 | 19.5 |

EXAMPLE 49

Coupling of thiolated AP to DVS-activated dextran. The influence of thiolated AP concentration Thiolated AP (SH-AP) was coupled to DVS-activated dextran of peak MW 500,000 with 1500 μmoles of vinyl groups per gram of dextran ("batch Dex-II"). The thiolated AP was produced as described in Example 45 and contained a mean of 1.7 moles of SH groups/mole of alkaline phosphatase.

The coupling procedure was as follows: Three different solutions (A–C) for coupling of thiolated AP to DVS-activated dextran were prepared to give the following final concentrations:

All solutions contained:

0.50M dipotassium hydrogen phosphate/hydrochloric acid (pH 8.0).

Solution A: 0.90 mg of SH-AP/ml; 0.129 mg of DVS-activated dextran/ml;

Solution B: 1.8 mg of SH-AP/ml; 0.258 mg of DVS-activated dextran/ml;

Solution C: 3.6 mg of SH-AP/ml; 0.516 mg of DVS-activated dextran.

The clear solutions were incubated at 24° C. with gentle shaking. Samples were withdrawn after different periods of incubation and the content of coupled thiolated AP was determined by gel filtration on Sephacryl™ S-300 HR. The results were as follows:

| Solution | 3 hours of incubation | | 24 hours of incubation | |
| --- | --- | --- | --- | --- |
| | coupling yield (%) | moles SH-AP/mole dextran | coupling yield (%) | moles SH-AP/mole dextran |
| A | 28 | 7.0 | 63 | 15.8 |
| B | 45 | 11.3 | 78 | 19.4 |
| C | 63 | 15.7 | 86 | 21.6 |

EXAMPLE 50

Coupling of thiolated AP to DVS-activated dextran. The influence of temperature

Thiolated AP (SH-AP) was coupled to DVS-activated dextran of peak MW 500,000 with 1500 μmoles of vinyl groups per gram of dextran ("batch Dex-II"). The thiolated AP was produced as described in Example 45 and contained a mean of 1.9 moles of SH groups/mole of alkaline phosphatase.

The coupling procedure was as follows: A solution for coupling of thiolated AP to DVS-activated dextran was prepared to give the following final concentrations:

1.9 mg of SH-AP/ml;

0.271 mg of DVS-activated dextran/ml;

0.50M dipotassium hydrogen phosphate/hydrochloric acid (pH 8.0).

The clear solution was divided into two samples of equal volume (A and B) which were then incubated for 22 hours with gentle shaking at the following temperatures:

Sample A: 24° C.

Sample B: 30° C.

The content of coupled thiolated AP was determined by gel filtration on Sephacryl™ S-300 HR, and the results were as follows:

| Sample | coupling yield (%) | moles SH-AP/mole dextran |
| --- | --- | --- |
| A | 71 | 17.7 |
| B | 75 | 18.7 |

EXAMPLE 51

Coupling of thiolated AP to DVS-activated dextran. The influence of the molar ratio between thiolated AP and DVS-activated dextran. High ratios Thiolated AP (SH-AP) was coupled to DVS-activated dextran of peak MW 500,000 with 1500 μmoles of vinyl groups per gram of dextran ("batch Dex-II"). The thiolated AP was produced as described in Example 45 and contained a mean of 1.9 moles of SH groups/mole of alkaline phosphatase.

The coupling procedure was as follows: Three different solutions (A–C) for coupling of thiolated AP to activated dextran were prepared to give the following final concentrations:

All solutions contained:

1.9 mg of SH-AP/ml;

0.50M dipotassium hydrogen phosphate/hydrochloric acid (pH 8.0).

Solution A: 0.543 mg of DVS-activated dextran/ml (SH-AP:dextran=12:1);

Solution B: 0.272 mg of DVS-activated dextran/ml (SH-AP:dextran=25:1);

Solution C: 0.136 mg of DVS-activated dextran/ml (SH-AP:dextran=50:1).

The clear solutions were incubated at 24° C. for 22 hours with gentle shaking.

The content of coupled thiolated AP was determined by gel filtration on Sephacryl™ S-300 HR, and the results were as follows:

| Solution | coupling yield (%) | moles SH-AP/mole dextran |
| --- | --- | --- |
| A | 89 | 11.1 |
| B | 71 | 17.7 |
| C | 42 | 21.0 |

EXAMPLE 52

Coupling of thiolated AP to DVS-activated dextran. The influence of the molar ratio between thiolated AP and activated dextran. Low ratios Thiolated AP (SH-AP) was coupled to DVS-activated dextran of peak MW 500,000 with 1500 μmoles of vinyl groups per gram of dextran ("batch Dex-II"). The thiolated AP was produced as described in Example 45 and contained a mean of 1.6 moles of SH groups/mole of alkaline phosphatase.

The coupling procedure was as follows: Three different solutions (A–C) for coupling of SH-alkaline phosphatase to DVS-activated dextran were prepared to give the following final concentrations:

All solutions contained:

1.8 mg of SH-AP/ml;

0.50M dipotassium hydrogen phosphate/hydrochloric acid (pH 8.0).

Solution A: 1.07 mg of DVS-activated dextran/ml (SH-AP:dextran=6:1);

Solution B: 0.536 mg of DVS-activated dextran/ml (SH-AP:dextran=12:1);

Solution C: 0.357 mg of DVS-activated dextran/ml (SH-AP:dextran=18:1).

The clear solutions were incubated at 24° C. for 22 hours with gentle shaking.

The content of coupled thiolated AP was determined by gel filtration on Sephacryl™ S-300 HR, and the results were as follows:

| Solution | coupling yield (%) | moles SH-AP/mole dextran |
| --- | --- | --- |
| A | 91 | 5.4 |
| B | 90 | 10.8 |
| C | 75 | 13.5 |

EXAMPLE 53

Coupling of thiolated AP to antibody-dextran. The influence of pH

Thiolated AP (SH-AP) was coupled to antibody-dextran [produced as described in Example 25, sample B, and containing 10 moles of antibody (goat anti mouse) per mole of dextran]. The thiolated AP was produced as described in Example 45 and contained a mean of 1.4 moles of SH groups/mole of alkaline phosphatase.

The coupling procedure was as follows: Two different solutions for coupling of thiolated AP to antibody-dextran were prepared to give the following final concentrations:

Both solutions contained:
0.94 mg of thiolated AP/ml;
0.134 mg of dextran/ml;
0.50M dipotassium hydrogen phosphate/hydrochloric acid.

The pH values of the dipotassium hydrogen phosphate buffers were:
Solution A: pH 7.0
Solution B: pH 8.0.

The clear solutions were incubated at 24° C. for 22 hours with gentle shaking.

The content of coupled thiolated AP was determined by gel filtration on Sephacryl™ S-300 HR, and the results were as follows:

| Solution | coupling yield (%) | moles SH-AP/mole dextran |
|---|---|---|
| A | <1 | 0.2 |
| B | 20 | 5.0 |

EXAMPLE 54

Coupling of thiolated antibody to alkaline phosphatase-dextran

Goat anti mouse Ig (GAM) (DAKO A/S, Denmark, cat. No. Z420) was thiolated with N-succinimidyl-3-(2-pyridyldithio)propionate (SPDP) (Pharmacia, cat. No. 17-0458-01) and then coupled to two different alkaline phosphatase-dextran (AP-dextran) preparations. The first AP-dextran was prepared as described in Example 52, solution B, and contained 11 moles of alkaline phosphatase per mole of dextran; the second was prepared as described in Example 51, solution B, and contained 18 moles of alkaline phosphatase per mole of dextran. The thiolated antibody was prepared according to the general procedure for thiolation of proteins first described by Carlsson et al., *Biochem. J.* (1978) 173 723–737, and contained a mean of 4 moles of SH groups/mole of goat anti mouse antibody.

The procedure for coupling the thiolated goat anti mouse Ig (SH-GAM) was as follows: Four solutions for coupling of SH-GAM to AP-dextran were prepared to give the following final concentrations:

All solutions contained:
2.0 mg SH-GAM/ml;
0.50M dipotassium hydrogen phosphate/hydrochloric acid (pH 8.0).

A and B: 10 moles of alkaline phosphatase/mole of dextran;
C and D: 18 moles of alkaline phosphatase/mole of dextran;
A: AP-dextran corresponding to 0.516 mg dextran/ml;
B: AP-dextran corresponding to 0.258 mg dextran/ml;
C: AP-dextran corresponding to 0.516 mg dextran/ml;
D: AP-dextran corresponding to 0.258 mg dextran/ml.

The clear solutions were incubated at 24° C. for 22 hours with gentle shaking.

The degree of coupling of SH-GAM was determined by gel filtration on Sephacryl™ S-300HR, and the results were as follows:

| Solution | coupling yield (%) | moles SH-GAM/mole dextran |
|---|---|---|
| A | 78 | 9.8 |
| B | 49 | 12.2 |
| C | —* | — |
| D | —* | — |

*precipitation of a gel occurred in the reaction vessels for samples C and D.

EXAMPLE 55

Coupling of monoclonal murine antibody co horseradish peroxidase-dextran

Protein A purified mouse anti human kappa light chains (DAKO A/S, Denmark, cat. No. M 827) was coupled to HRP-dextran. The HRP-dextran was prepared as described in Example 12 (48 hours of incubation, 4° C.). The HRP-dextran contained 16 moles of horseradish peroxidase per mole of dextran.

The coupling procedure was as follows: Three different solutions (A–C) for coupling mouse anti human kappa light chains to HRP-dextran were prepared to give the following final concentrations:

All samples contained:
HRP-dextran corresponding to 0.30 mg of dextran/ml;
2.74 mg of mouse anti human kappa light chains/ml;
0.7M dipotassium hydrogen phosphate titrated with either hydrochloric acid or sodium hydroxide to:
A: pH 8.4
B: pH 9.2
C: pH 10.0.

The clear solutions were incubated at 24° C. without stirring for:
A: 24 hours,
B and C: 6 hours.

The content of coupled mouse anti human kappa light chains was determined by gel filtration on Sephacryl™ S-300 HR, and the results were as follows:

| Sample | coupling yield (%) | moles mouse anti human kappa light chains/mole dextran |
|---|---|---|
| A | 3.2 | 0.95 |
| B | 1.6 | 0.47 |
| C | 5.6 | 1.66 |

EXAMPLE 56

Complexes between murine monoclonal antibodies and dextran coupled with peroxidase and rabbit anti mouse Ig. The influence of different concentrations of monoclonal antibody Mouse anti human kappa light chains (DAKO A/S, Denmark, cat. No. M 827) were complexed with dextran coupled with horseradish peroxidase and rabbit anti mouse Ig (HRP-dextran/RAM). The latter were prepared as described in Example 36C, solution B.

Complex formation:
Seven different samples (A–G) for complex formation between mouse anti human kappa light chains and HRP-dextran/RAM were prepared to give the following final concentrations:

The samples contained:

HRP-dextran/RAM conjugate corresponding to 0.020 mg of dextran/ml and 0.042 mg of RAM/ml and A: 0.003 mg of mouse anti human kappa light chains/ml;
B: 0.006 mg of mouse anti human kappa light chains/ml;
C: 0.012 mg of mouse anti human kappa light chains/ml;
D: 0.030 mg of mouse anti human kappa light chains/ml;
E: 0.061 mg of mouse anti human kappa light chains/ml;
F: 0.121 mg of mouse anti human kappa light chains/ml;
G: 0.242 mg of mouse anti human kappa light chains/ml.

Complex formation was allowed to proceed at room temperature for 2 hours, and the samples were then tested in ELISA.

ELISA:

The ELISA was performed as a two-layer technique according to "General ELISA procedure".

First layer formed using: 5 μg/ml, 1 μg/ml, 0.2 μg/ml and 0.04 μg/ml, respectively, of human serum proteins in 0.01M sodium phosphate, 0.145M NaCl, pH 7.2;

Second layer: dilutions of the complexes (A–G) corresponding to 12 ng of dextran/ml (diluted in 0.01M sodium phosphate, 0.145M NaCl, 0.1% Tween™ 20, pH 7.2.

ortho-phenylenediamine/hydrogen peroxide was used as colour-development HRP substrate, with a reaction time of 10 minutes.

Figure 6:
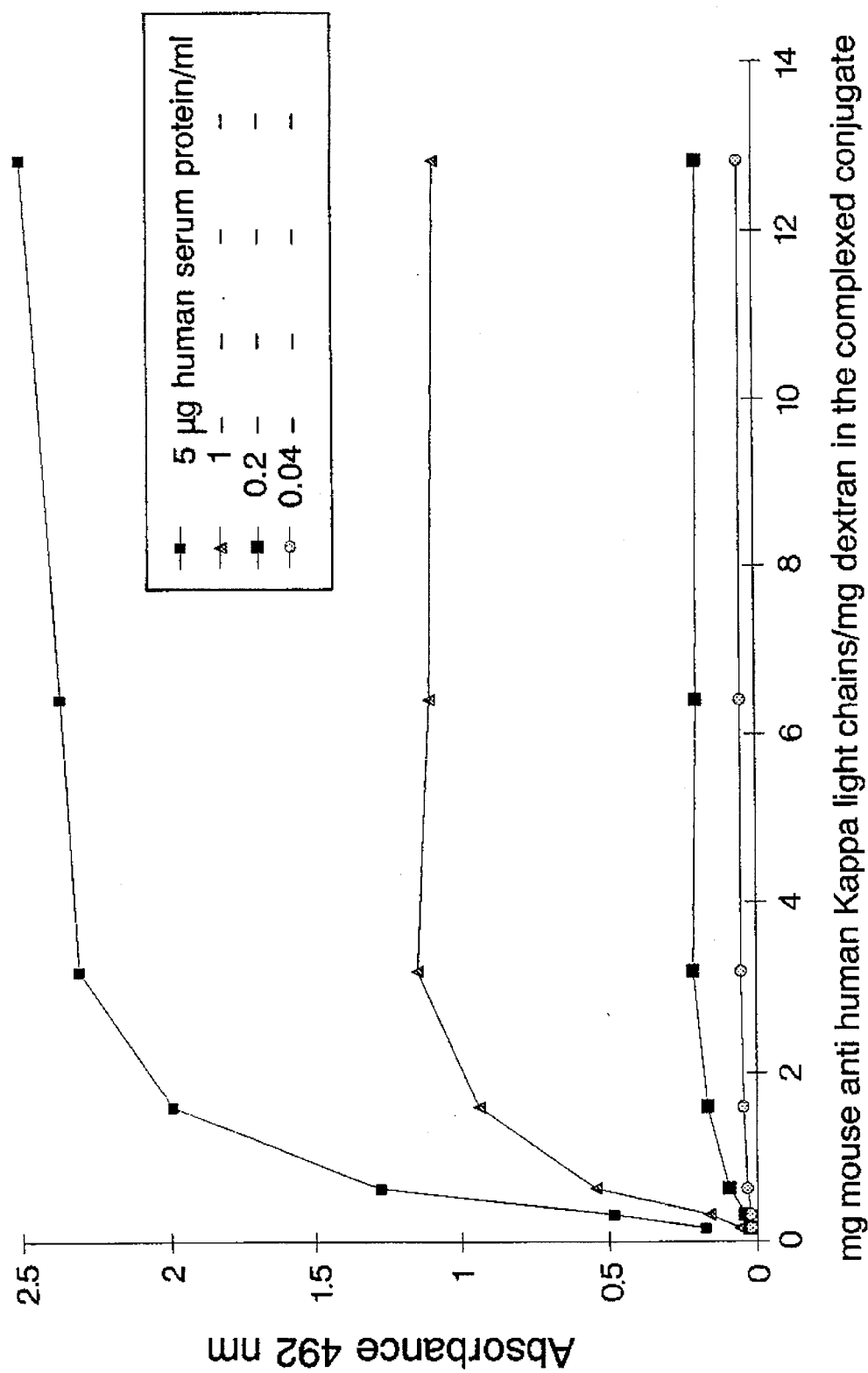
FIG. 6: Results from Example 56. Relationship between the ratio of mg of mouse anti human kappa light chains to mg of dextran (in a complex formed between mouse anti human kappa light chains and HRP-dextran/RAM conjugate) and the absorbance at 492 nm in a two-layer ELISA. Results are shown for four concentrations of human serum proteins used for the first layer (i.e. for adsorption to the surface of the solid-phase support). A levelling off of the absorbance is observed at a ratio of approximately 4 mg mouse anti human kappa light chains/mg dextran, independent of the concentration of human serum proteins used for adsorption to the solid-phase support.

Results:

The results of the ELISA analysis are shown in FIG. 6, which shows the absorbance at 492 nm obtained for each of the four concentrations of human serum proteins used for the first layer in the ELISA as a function of the ratio of mouse anti human kappa light chains to HRP-dextran/RAM conjugate used in the complex formation (expressed as mg of mouse anti human kappa light chains per mg of dextran in the conjugate).

As can be seen, the absorbance levels off at a ratio of about 4 mg of mouse anti human kappa light chains/mg of dextran.

EXAMPLE 57

Complexes formed between biotinylated rabbit polyclonal antibodies and high molecular weight dextran coupled with horseradish peroxidase and streptavidin Purified rabbit anti human kappa light chains (DAKO A/S, Denmark, cat. No. A192) were biotinylated with N-biotinyl-ε-amino-caproic acid N-hydroxysuccinimide ester (Sigma, cat. No. B 2643) according to Kendall et al., *Journal of Immunological Methods* (1983) 56 329–339. 0.04 μmoles of biotin were used per mg of protein.

The biotinylated rabbit anti human kappa light chains were then complexed with the high molecular weight dextran coupled with horseradish peroxidase and streptavidin (HRP-dextran/streptavidin). The HRP-dextran/streptavidin was prepared as described in Example 39.

Complex formation:

Three different samples (A–C) for complex formation between biotinylated rabbit anti human kappa light chains and HRP-dextran/streptavidin were prepared to give the following final concentrations:

All samples contained:

HRP-dextran/streptavidin conjugate corresponding to 0.2 mg of dextran/ml and 0.12 mg of streptavidin/ml.

A: 0.156 mg of biotinylated rabbit anti human kappa light chains/ml;
B: 0.309 mg of biotinylated rabbit anti human kappa light chains/ml;
C: 0.465 mg of biotinylated rabbit anti human kappa light chains/ml.

Complex formation was allowed to proceed at room temperature for 2 hours, and the samples were then tested in an ELISA and in an immunohistochemical procedure.

ELISA:

The ELISA was performed as a two-layer technique according to the following procedure:

First layer formed using: 5 μg of human serum proteins/ml, diluted in 0.01M sodium phosphate, 0.145M NaCl, pH 7.2;

Second layer: six serial dilutions of each of the complex samples (A–C) containing between 2 μg of dextran/ml and 0.0625 μg of dextran/ml (diluted in 0.01M sodium phosphate, 0.145M NaCl, 0.1% Tween™ 20, pH 7.2.

ortho-phenylenediamine/hydrogen peroxide was used as colour-development HRP substrate, with a reaction time of 2 minutes.

Figure 7:
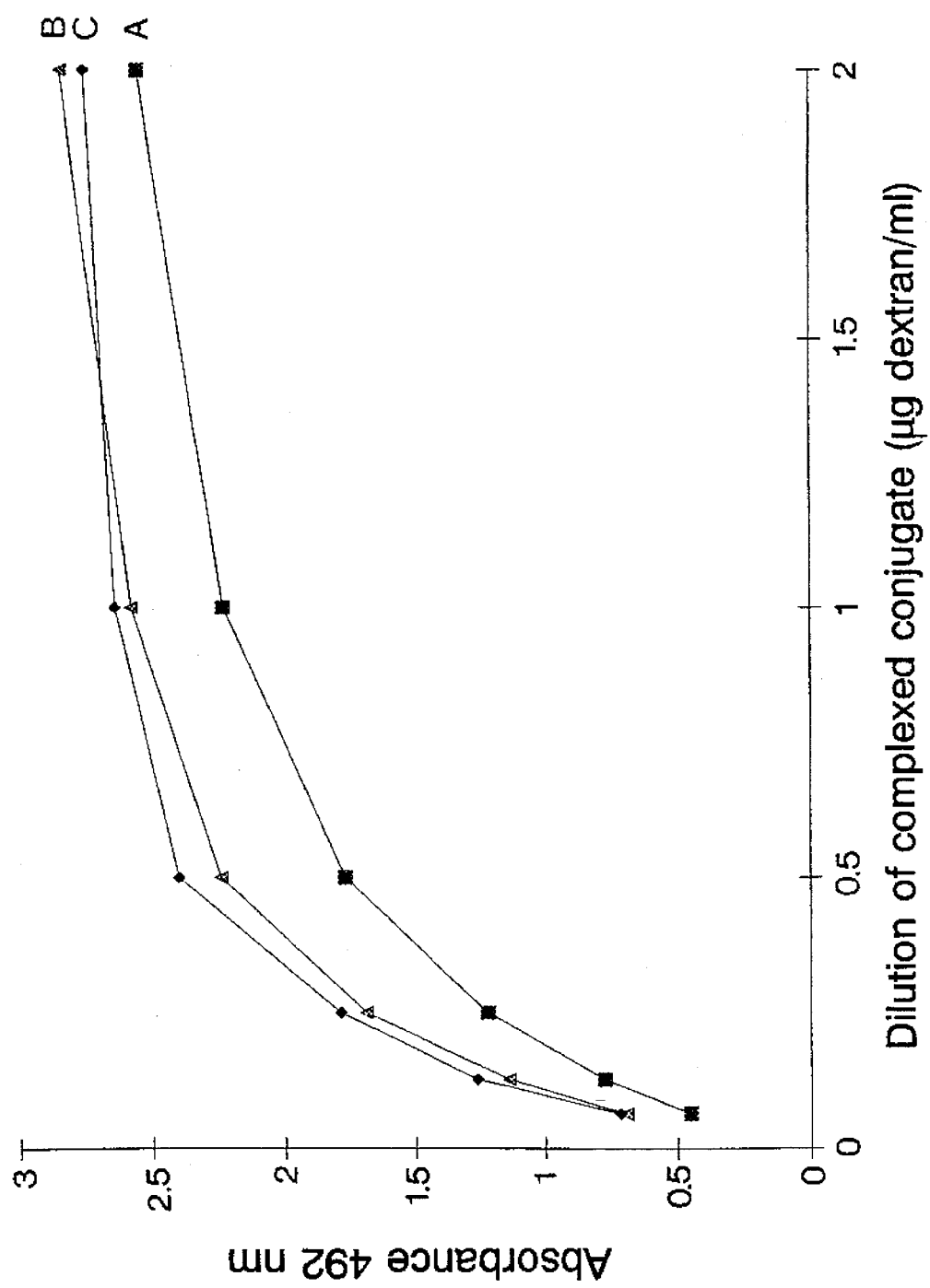
FIG. 7: Results from Example 57. Relationship between the concentration of dextran (in a complex formed between biotinylated rabbit anti human kappa light chains and HRP-dextran/streptavidin conjugate) and the absorbance at 492 nm in a two-layer ELISA. Results are shown for complexes formed at three different concentrations of biotinylated rabbit anti human kappa light chains. It is apparent that for a given concentration of complexed conjugate, a maximum absorbance value is obtained when the complex is formed using a concentration of about 0.309–0.465 mg of biotinylated rabbit anti human kappa light chains/ml.

Results:

The results of the ELISA analysis are shown in FIG. 7, which shows the absorbance at 492 nm obtained for each of the three samples (A–C) as a function of the dilution of each complexed conjugate.

As can be seen, for a given concentration of complexed conjugate the absorbance attained a maximum value when the complex had been formed using a concentration of about 0.309–0.465 mg of biotinylated rabbit anti human kappa light chains/ml.

Immunohistochemistry:

The immunohistochemical analysis was performed according to "Handbook, Immunochemical Staining Methods", Sally J. Naish, DAKO Corporation, 1989.

The complexes in samples A–C were tested on tonsil tissue sections, each sample being diluted to concentrations in the range corresponding to 0.1–0.0125 mg of dextran/ml.

Diaminobenzidine tetrahydrochloride (DAB)/hydrogen peroxide was used as colour-development HRP substrate.

As control method, a three-step LSAB method (described in "Handbook, Immunochemical staining methods", DAKO Corporation, 1989) was employed.

The following results were obtained:

| Sample | score |
| --- | --- |
| A | ++ |
| B | ++(+) |
| C | ++(+) |
| LSAB | +++ |

Results:

The results of the immunohistochemical analysis show that at the concentration level employed, the three-step LSAB method is only slightly better than the one-step method based on the present complexes formed between HRP-dextran/-streptavidin conjugate and biotinylated rabbit anti human kappa light chains. It is thus possible, using a complexed conjugate according to the present invention, to simplify such an immunohistochemical analysis considerably and yet still achieve very satisfactory staining.

EXAMPLE 58

Complexes formed between murine monoclonal antibodies and dextran coupled with horseradish peroxidase and rabbit anti mouse IgG. The influence of concentration Mouse anti human kappa light chains (DAKO A/S, Denmark, cat. No. M 827) was complexed with dextran coupled with horseradish peroxidase and rabbit anti mouse IgG (HRP-dextran/RAM). The HRP-dextran/RAM preparation was prepared as described in Example 36C, solution B.

Complex formation:

Five different samples (A–E) were prepared by mixing a constant amount of HRP-dextran/Ram with a constant amount of mouse anti human kappa light chains in different final volumes. Samples with the following final concentrations of mouse anti human kappa light chains were prepared:

A: 0.280 mg/ml;
B: 0.140 mg/ml;
C: 0.093 mg/ml;
D: 0.070 mg/ml;
E: 0.056 mg/ml.

The clear solutions were incubated for 2 hours at room temperature before being tested in an ELISA and immunohistochemically.

ELISA:

The ELISA was performed as a two-layer technique according to the following procedure:

First layer formed using: 5 μg of human serum proteins/ml, diluted in 0.01M sodium phosphate, 0.145M NaCl, 0.1% Tween™ 20, pH 7.2;

Second layer: five serial dilutions of each of the complex samples (A–E) containing between 0.01 and 0.00013 μg of mouse anti human kappa light chains/ml (diluted in 0.01M sodium phosphate, 0.145M NaCl, 0.1% Tween™ 20, pH 7.2).

ortho-phenylenediamine/hydrogen peroxide was used as colour-development HRP substrate, with a reaction time of 10 minutes.

Figure 8:
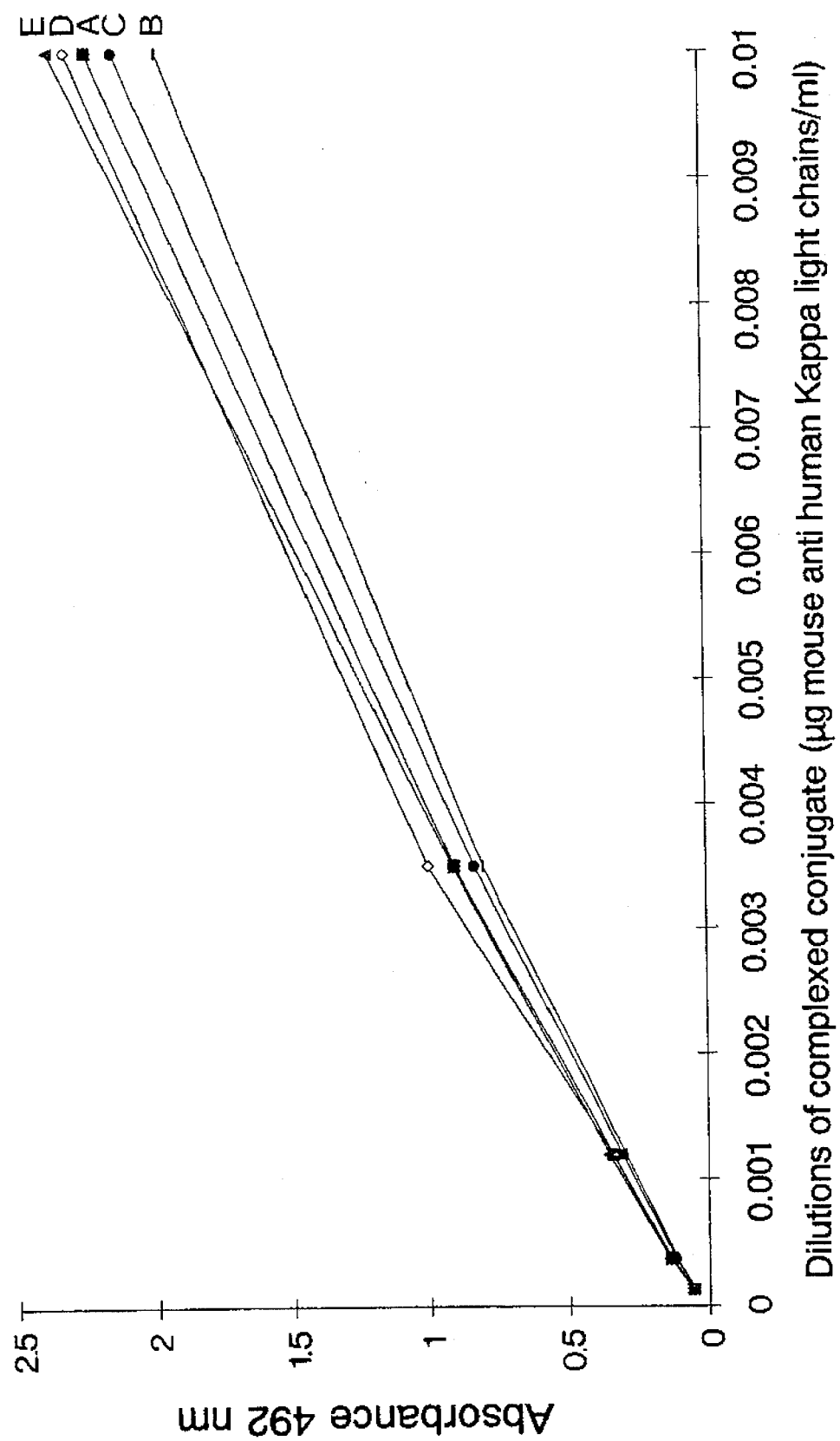
FIG. 8: Results from Example 58. Relationship between the concentration of mouse anti human kappa light chains (in a complex formed between mouse anti human kappa light chains and HRP-dextran/RAM conjugate) and the absorbance at 492 nm in a two-layer ELISA. Results are shown for complexes formed at five different concentrations of mouse anti human kappa light chains, keeping the ratio between mouse anti human kappa light chains and RAM constant during complex formation. The measured absorbance shows only small variations as a function of the concentration of mouse anti human kappa light chains used for complex formation.

Results:

The results of the ELISA analysis are shown in FIG. 8, which shows the absorbance at 492 nm obtained for each of the five samples (A–E) as a function of the concentration of the mouse anti human kappa light chains in each complexed conjugate sample.

As can be seen, the absorbance value for each of the samples (A–E) at a given concentration of mouse anti human kappa light chains shows only a relatively small variation; this indicates that at the concentrations employed, the volume in which the complexes are formed is of only minor influence.

Immunohistochemistry:

The immunohistochemical analysis was performed according to "Handbook, Immunochemical Staining Methods", Sally J. Naish, DAKO Corporation, 1989.

The samples were tested on tonsil tissue sections, each sample being diluted to concentrations in the range corresponding to 0.028–0.0035 mg of mouse anti human kappa light chains/ml.

Diaminobenzidine tetrahydrochloride (DAB)/hydrogen peroxide was used as colour-development HRP substrate.

For control purposes, a conventional conjugate, i.e. horseradish peroxidase-labelled rabbit anti human kappa light chains (DAKO A/S, Denmark, cat. No. P129), was employed, diluted in accordance with the manufacturers recommendations, and the LSAB method ("Handbook, Immunochemical Staining Methods", DAKO Corporation, 1989) was also used.

The following results were obtained:

| Sample | score |
| --- | --- |
| A | ++++ |
| B | ++++ |
| C | ++++ |
| D | ++++ |
| E | +++(+) |
| conventional conjugate | ++(+) |
| LSAB | +++(+) |

Results:

The results of the immunohistochemical analysis show that the one-step method based on the present complexes formed between HRP-dextran/RAM conjugate and mouse anti human kappa light chains is slightly better than the three-step LSAB method and significantly better than the one-step method based on the conventional conjugate. This again illustrates the advantages associated with the use of a complexed conjugate according to the present invention with regard to the simplicity of the analysis set-up and the staining intensity obtainable.

We claim:

1. A water-soluble reagent comprising a water-soluble polymeric carrier molecule having attached thereto more than one connecting moiety of the formula

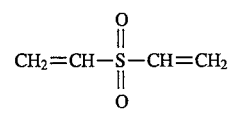

wherein (1) the connecting moiety is derived from divinyl sulfone, (2) each connecting moiety is attached to a reactive functional group on the polymeric molecule via a covalent linkage formed between one of the two vinyl groups of the connecting moiety and the reactive functional group on the polymeric molecule, (3) the content of free reactive terminal vinyl groups is in the range of from about 50 to about 5,000 μmoles of vinyl groups per gram of polymeric carrier, (4) the reagent is capable of reaction with a molecular species having a functional group which is reactive towards the terminal vinyl group of the more than one connecting moiety, and (5) the molecular species is selected from the group consisting of labelling species, marking species, and targeting species.

2. A reagent according to claim 1, wherein the polymeric carrier is selected from the group consisting of natural and synthetic polysaccharides, homopoly amino acids, natural and synthetic polypeptides and proteins, and synthetic polymers having nucleophilic functional groups.

3. A reagent according to claim 1, wherein the polymeric carrier is selected from the group consisting of polyvinyl alcohols, polyallyl alcohols, polyethylene glycols and substituted polyacrylates.

4. A reagent according to claim 1, wherein the polymeric carrier is selected from the group consisting of dextrans, carboxymethyl-dextrans, starches, hydroxyethyl-starches, hydroxypropyl-starches, glycogen, agarose derivatives, cellulose derivatives and natural gums.

5. A reagent according to claim 1, wherein the polymeric carrier is selected from the group consisting of hydroxyethyl-celluloses and hydroxypropyl-celluloses.

6. A water-soluble conjugate obtained by reaction of a water-soluble reagent according to claim 1 with a molecular species which is different from the polymeric carrier molecule wherein the molecular species is selected from the group consisting of labelling species, marking species and targeting species, and wherein the conjugate has more than one molecule covalently attached thereto each via a connecting group derived from a terminal vinyl group of the water-soluble reagent.

7. A conjugate according to claim 6 having a content of from 2 to 500 of remaining free reactive terminal vinyl groups capable of reaction with a molecular species.

8. A conjugate according to claims 6 or 7, wherein the molecular species is selected from the group consisting of proteins; enzymes; toxins; drugs; dyes; fluorescent, luminescent, phosphorescent and other light-emitting substances; metal-chelating substances; substances labelled with a radioactive isotope; and substances labelled with a heavy atom.

9. A conjugate according to claims 6 or 7, wherein the molecular species is selected from the group consisting of ferritin, phycoerythrins, phycocyanins, phycobilins, horseradish peroxidase, alkaline phosphatase, glucose oxidases, galactosidases, ureases, iminodiacetic acid, ethylenediaminetetraacetic acid, diethylenetriaminepentaacetic acid, and desferrioxamine B.

10. A conjugate according to claims 6 or 7, wherein the molecular species is a targeting species selected from the group consisting of: antigens; haptens; monoclonal and polyclonal antibodies; gene probes; natural and synthetic oligo- and polynucleotides; natural and synthetic mono-, oligo- and polysaccharides; lectins; avidin and streptavidin; biotin; growth factors; hormones; receptor molecules; protein A and protein G.

11. A conjugate according to claims 6 or 7, wherein the molecular species of the conjugate are of at least two different types.

12. A conjugate according to claim 6, wherein the polymeric carrier is selected from the group consisting of natural and synthetic polysaccharides; homopoly amino acids; natural and synthetic polypeptides and proteins; and synthetic polymers having nucleophilic functional groups.

13. A conjugate according to claim 6, wherein the polymeric carrier is selected from the group consisting of polyvinyl alcohols, polyallyl alcohols, polyethylene glycols and substituted polyacrylates.

14. A conjugate according to claim 6, wherein the polymeric carrier is selected from the group consisting of dextrans, carboxymethyl-dextrans, starches, hydroxyethyl-starches, hydroxypropyl-starches, glycogen, agarose derivatives, cellulose derivatives and natural gums.

15. A conjugate according to claim 1, wherein the polymeric carrier is selected from the group consisting of hydroxyethyl-celluloses and hydroxypropyl-celluloses.

* * * * *

UNITED STATES PATENT AND TRADEMARK OFFICE
CERTIFICATE OF CORRECTION

PATENT NO. : 5,543,332
DATED : August 6, 1996
INVENTOR(S) : Allan Otto Fog LIHME et al.

It is certified that error appears in the above-identified patent and that said Letters Patent is hereby corrected as shown below:

Column 60, line 19, claim 15: Delete "1" and insert --6--.

Signed and Sealed this

First Day of September, 1998

Attest:

BRUCE LEHMAN

Attesting Officer

Commissioner of Patents and Trademarks